US011690591B2

(12) United States Patent
Oura

(10) Patent No.: US 11,690,591 B2
(45) Date of Patent: Jul. 4, 2023

(54) APPARATUS AND METHODS FOR DETECTING INCREASE IN BRAIN SWELLING AND/OR SHIFTING

(71) Applicant: NIHON KOHDEN CORPORATION, Tokyo (JP)

(72) Inventor: Mitsuhiro Oura, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 830 days.

(21) Appl. No.: 15/763,093

(22) PCT Filed: Sep. 24, 2016

(86) PCT No.: PCT/IB2016/055723
§ 371 (c)(1),
(2) Date: Mar. 23, 2018

(87) PCT Pub. No.: WO2017/051388
PCT Pub. Date: Mar. 30, 2017

(65) Prior Publication Data
US 2018/0214117 A1    Aug. 2, 2018

Related U.S. Application Data

(60) Provisional application No. 62/232,019, filed on Sep. 24, 2015.

(51) Int. Cl.
*A61B 8/00* (2006.01)
*A61B 8/08* (2006.01)
(52) U.S. Cl.
CPC .......... *A61B 8/0816* (2013.01); *A61B 8/4227* (2013.01); *A61B 8/4427* (2013.01);
(Continued)

(58) Field of Classification Search
CPC .............................. A61B 8/0816; A61B 8/488
See application file for complete search history.

(56) References Cited

U.S. PATENT DOCUMENTS

| 5,590,649 A * | 1/1997 | Caro ................. A61B 5/02108 600/300 |
| 5,951,476 A | 9/1999 | Beach |
| 2002/0095087 A1 | 7/2002 | Mourad et al. |
| 2004/0059220 A1 | 3/2004 | Mourad et al. |

(Continued)

FOREIGN PATENT DOCUMENTS

| JP | H10-179527 A | 7/1998 |
| JP | H11-276446 A | 10/1999 |

(Continued)

OTHER PUBLICATIONS

International Search Report and Written Opinion of the International Search Report for PCT/IB2016/055723 dated Dec. 14, 2016.

(Continued)

*Primary Examiner* — Joseph M Santos Rodriguez
(74) *Attorney, Agent, or Firm* — Kenealy Vaidya LLP

(57) ABSTRACT

The disclosed subject matter related to methods and apparatus for determining brain swelling and brain shifting in a patient as well as predicting a possible resultant increase in intracranial pressure in the patient. The apparatus can include a transducer such as an ultrasound transducer communicatively connected to a controller via wires or via wireless communications device(s). A monitor and/or alarm device can be provided to notify a practitioner when the controller has determined brain swelling is occurring and/or when an imminent increase in intracranial pressure is likely to occur.

19 Claims, 18 Drawing Sheets

(52) U.S. Cl.
CPC ............ *A61B 8/488* (2013.01); *A61B 8/5223* (2013.01); *A61B 8/5269* (2013.01); *A61B 8/5284* (2013.01)

(56) References Cited

U.S. PATENT DOCUMENTS

| | | |
|---|---|---|
| 2005/0015009 A1 | 1/2005 | Mourad et al. |
| 2006/0079773 A1 | 4/2006 | Mourad et al. |
| 2006/0100530 A1 | 5/2006 | Kilot et al. |
| 2007/0016031 A1 | 1/2007 | Mourad et al. |
| 2008/0275340 A1 | 11/2008 | Beach et al. |
| 2009/0149751 A1 | 6/2009 | Mourad et al. |
| 2010/0081893 A1 | 4/2010 | Jarvik et al. |
| 2010/0087728 A1 | 4/2010 | Jarvik et al. |
| 2012/0108918 A1 | 5/2012 | Jarvik et al. |
| 2014/0039279 A1 | 2/2014 | Jarvik et al. |
| 2017/0319099 A1* | 11/2017 | Levinson ............. A61B 5/7214 |

FOREIGN PATENT DOCUMENTS

| | | |
|---|---|---|
| JP | 2002-159492 A | 6/2002 |
| JP | 2004-520870 A | 7/2004 |
| JP | 2006-526487 A | 11/2006 |
| KR | 20070077837 A | 7/2007 |
| WO | 0243564 A2 | 6/2002 |

OTHER PUBLICATIONS

U.S. Department of Health and Human Services, "Intensive care units for newborns in nine States see sharp drop in bloodstream infections," Mar. 2013, No. 391, pp. 1-36, AHRQ, Silver Spring, MD.

Papa, L., et al., "Serum levels of Ubiquitin C-terminal Hydrolase (UCH-L1) distinguish mild traumatic brain injury (TBI) from trauma controls and are elevated in mild and moderate TBI patients with intracranial lesions and neurosurgical intervention," J Trauma Acute Care Surg., May 2012, 72(5), pp. 1335-1344.

Biogeau, J., et al., "Ultrasound Tissue Pulsatility Imaging Suggests Impairment in Global Brain Pulsatility and Small Vessels in Elderly Patients with Orthostatic Hypotension," Journal of Stroke and Cerebrovascular Diseases, 2016, pp. 1-6.

Desmidt, T., et al., "Ultrasound Brain Tissue Pulsatility is decreased in middle aged and elderly type 2 fiabetic patients with depression," Psychiatry Research: Neuroimaging, 2011, 193, pp. 63-64, Seattle, WA.

Desmidt, T., et al., "Brain Tissue Pulsatility is Increased in Midlife Depression: a Comparative Study Using Ultrasound Tissue Pulsatility Imaging," Neuropsychopharmacology, 2017, pp. 1-8.

Kucewicz, J. C., et al., "Functional Tissue Pulsatility Imaging of the Brain during Visual Stimulation," Ultrasound Med Biol, May 2007, 33(5), pp. 681-690, Seattle, WA.

Kucewicz, J. C., et al., "Tissue Pulsatility Imaging of Cerebral Vasoreactivity during Hyperventilation," Ultrasound Med Biol, Aug. 2008, 34(8), pp. 1200-1208, Seattle, WA.

Ternifi, R., et al., "Ultrasound measurements of brain tissue pulsatility correlate with the volume of MRI white-matter hyperintensity," Journal of Cerebral Blood Flow & Metabolism, 2014, 34, pp. 942-944.

Moehring, M. A., et al., "Intracranial Bleed Monitor," IEEE Ultrasonics Symposium, 1999, pp. 1545-1549, Seattle, WA.

"Guideline for the Management of Severe Traumatic Brain Injury 3rd Edition," Brain Trauma Foundation, Inc, 2007, pp. S1-S106, New York, NY.

Japanese Office Action for the related Japanese Patent Application No. 2018-515243 dated Oct. 12, 2020.

European Office Action for the related European Patent Application No. 16 778 460.2 dated Aug. 8, 2019.

Japanese Office Action for the related Japanese Patent Application No. 2021-144595 dated Sep. 7, 2022.

* cited by examiner

APPARATUS AND METHODS FOR DETECTING INCREASE IN BRAIN SWELLING AND/OR SHIFTING

CROSS-REFERENCE TO RELATED APPLICATIONS

This application is a U.S. National Stage Application under 35 U.S.C § 371 of International Patent Application No. PCT/IB2016/055723 filed 24 Sep. 2016, which claims the benefit of priority to U.S. Provisional Application No. 62/232,019 filed 24 Sep. 2015, the disclosures of all of which are hereby incorporated by reference in their entireties.

BACKGROUND

The disclosed subject matter relates to methods, kits, and devices for detecting swelling of the brain in a patient. More particularly, the disclosed subject matter relates to methods, kits and devices configured for ensuring easy and continuous procedures for identifying intracranial tissue swelling in order to predict when an increase in intracranial pressure (ICP) will occur. Increased ICP can arise as a consequence of various traumas, diseases or congenital defects, and can be a result of intracranial mass lesions, disorders of cerebrospinal fluid (CSF) circulation, as well as more diffuse intracranial pathological processes. For example, in some cases, increased ICP is caused by obstruction of the outflow of Cerebral Spinal Fluid (CSF). This obstruction causes the ventricles to expand resulting in hydrocephalus.

In another example, a stroke or head trauma patient's brain tissue might gradually swell or shift after onset of symptoms, and this can cause what is commonly referred to as "second brain injury." Second brain injury can lead to brain herniation, hypercapnia, acidosis, meningitis, brain abscess and other serious injuries. Thus, the need for continuous, non-invasive, and yet cost effective and practical monitoring has been present in the medical field.

To avoid second brain injury, brain monitoring is typically conducted. Frequent and repeated computerized tomography (CT) scans and/or intracranial pressure (ICP) monitoring is typically recommended by head trauma guidelines in order to assess brain tissue condition.

The brain typically includes four fluid-filled ventricles that are connected. These cavities, known collectively as the ventricular system, include or consist of the left and right lateral ventricles, the third ventricle, and the fourth ventricle. The fourth ventricle extends from the cerebral aqueduct (aqueduct of Sylvius) to the obex, and is filled with CSF. The fourth ventricle has a characteristic diamond shape in cross-sections of the human brain. The fourth ventricle is located within the pons or in the upper part of the medulla. CSF entering the fourth ventricle through the cerebral aqueduct can exit to the subarachnoid space of the spinal cord through two lateral foramina of Luschka and a single, midline foramen of Magendie.

The fourth ventricle is an outpouching on the posterior part of the brainstem. The flow of CSF to the nasal submucosal lymphatic channels occurs through the cribriform. When CSF pressure is elevated, cerebral blood flow may be constricted. CSF entering the fourth ventricle through the cerebral aqueduct can exit to the roof of the fourth ventricle formed by the cerebellum (and can expand into lateral, third and fourth ventricles, connected by thinner channels). Expansion of the ventricles is called Hydrocephalus and can lead to an increase in intracranial pressure. Congenital hydrocephalus is present in about 0.1% of newborn children and is due to outflow obstruction. Acquired Normal Pressure Hydrocephalus (NPH), due to excessive production of CSF, is present in an estimated 0.5% of adults over the age of 65, is underdiagnosed, and can cause gait disturbances, urinary incontinence and dementia.

Alternatively, expansion of intracranial solid tissues including: [1] brain cell swelling (cerebral edema) from infectious, hemodynamic, pharmacologic, metabolic or traumatic causes, [2] brain tumors, and [3] subdural or epidural hematomas from minor head trauma, can cause collapse of the ventricles; continued expansion results in increased ICP.

In both hydrocephalus (ventricular inflation) and intracranial tissue expansion, the first compensation is the obliteration of the layer of CSF surrounding the brain. The obliteration of this layer typically precedes an increase in ICP.

While normal ranges for ICP vary with age, increases in ICP can be acute or chronic, and thresholds for treatment are often difficult to determine.

The relation between volume and pressure within the cranium is non-linear. The Monro-Kellie hypothesis states that the sum of the intracranial volumes of blood, brain, CSF, and other components (for example, tumor, hematoma) is constant. The skull can be considered to be an inelastic container. An increase in the volume of any one of the intracranial contents is typically offset by a decrease in one or more of the others, ultimately leading to an increase in ICP. Intracranial blood (especially in the venous/venular compartment) and CSF are two low pressure components whose volume can adapt easily to accommodate an increase in the volume of intracranial contents. Once the change in volumes of intracranial blood and CSF are exhausted, further increases in volume result in increase in ICP. Changes in both arterial and venous compartments affect pressure. Sitting up to an inclined position to raise the brain 20 cm above the heart results in ICP reduction by 8 mmHg due to deflation of the veins and venules; the expansion of intracranial arteries and arterioles by about 5 milliliters after each heart beat raises ICP by 1 mmHg. Compliance (the change in volume for a given change in pressure) provides an index of compensatory reserve, with low values suggesting a diminished reserve. Compliance is reduced when ICP is elevated, at an abnormal ICP of 25 mmHg, the arterial pressure ICP pulsation is 4 mmHg.

ICP monitoring is recommended by guideline to avoid the above-referenced "second brain injury." Although an ICP monitor can be continuously measured at a patient's bedside, there are several problems with this procedure/method. First, ICP mentoring is an invasive procedure. As shown in FIGS. 1A and 1B, the standard methods for clinical monitoring of ICP are all invasive, requiring a hole drilled in the skull and the placement of a pressure probe or catheter into the brain tissue.

Conventionally, emergency room personnel and intensive care practitioners could deliver better care if ICP could be measured or monitored in a patient presenting with certain conditions such as head trauma or neurological symptoms. Unfortunately, as described above, monitoring ICP is typically accomplished through the use of a manometer that is inserted into a hole drilled into the skull of the patient. Thus, monitoring ICP requires an invasive procedure undertaken by a neurosurgeon (or at least with a neurosurgeon available in case of complications or difficulties with the surgery), because the procedure exposes the patient to infection and other inherent surgical risks. In addition to the difficulty in obtaining and monitoring ICP, there are also certain drawbacks to relying solely on ICP for diagnosis and treatment of trauma. For example, relying solely on ICP data may cause a time delay in treatment, may require complicated diagnostic and monitoring protocols, and may be subject to false readings should the instrumentation for monitoring ICP not be set up correctly or otherwise fail or be interpreted improperly.

Anther problem with ICP monitoring is the ICP and intracranial volume relationship. FIG. 2 shows the ICP and intracranial volume curve. Medical guidelines for traumatic brain injury suggest maintaining ICP below 20-25 mmHg [Guidelines for the management of severe traumatic brain injury. J. Neurotrauma 24, S1-S106 (2007)]. However, as shown in FIG. 1A, even though intracranial volume is increased gradually, the ICP value is substantially stable until a critical point shown by arrow in FIG. 1A. After the critical point, the ICP increases dramatically. Therefore, it is difficult to maintain ICP below 20 mmHg. Accordingly a new method and device that can assess the brain condition before rising ICP has been sought after and desired.

CT scans have also been commonly used to assess the brain condition in a patient. Because a CT image can show the patient's intracranial brain "shape", CT is one of the most useful and reliable diagnosis methods for traumatic brain injury. Most traumatic brain injury patients are prescribed a CT-scan when each of the patients comes into the hospital, and additionally a follow-up CT scan is generally required.

One problem with the CT scan is that CT is not a "continuous" monitor and is not typically used at a patient's bedside. As described above, stroke or head trauma patients' brain tissue might gradually swell or shift after onset of symptoms. Even though frequent CT scans might be able to avoid second brain injury [N Engl J Med. 2012 Dec. 27; 367(26)2012 Dec. 12], realistically, frequent CT scans are not feasible because the patient is typically moved to a CT scan room, and this would have risk associated with patient transfer, such as patient cable problems or infection. Additionally, repeat CT imaging can increase radiation exposure and costs [http://www.ahrq.gov/news/newsletters/research-activities/13mar/0313RA13.html] [J Trauma Acute Care Surg. 2012 May; 72(5):1255-62.].

SUMMARY

Although ICP is an important variable for patient management, it is equally valuable to understand and possibly monitor and/or determine any causative variables associated with increases in ICP. Increases in ICP can be caused, in certain instances, by swelling of the brain tissues (edema) or by the expansion of tissue in the brain, for example, due to infection, injury, tumor, blood clot, or obstruction of cerebrospinal fluid (CSF) flow (hydrocephalus). Monitoring of brain swelling, other intracranial tissue swelling and/or ventricular expansion can provide information helpful in predicting an imminent increase in ICP, as well as extent of ICP increase, and can therefore provide a practitioner timely information to initiate therapy and to monitor the effectiveness of that therapy.

Swelling or enlarging of the brain will occur substantially freely within an approximately 1 mm thick cushion of cerebral fluid that surrounds the brain. However, after a point at which the brain either fills the calvarium, or meets resistance at an anchor or tether point, the brain runs out of room to further expand or swell, and ICP will then begin to increase. It is at this point, when the brain meets resistance from the skull or tether points in the skull, that motion of the brain with respect to the boundaries due to swelling will decrease. This decrease in relative motion of the brain can then be used as an indicator that ICP will soon increase.

In one exemplary method according to the disclosed subject matter, the potential for using Doppler ultrasound to assess brain swelling/shifting is used, especially but not exclusively in patients with suspected stroke or head injury at bedside. Doppler ultrasound is a safe, possibly portable, continuous monitoring technique, which is already used to monitor blood flow through the major arteries, but has not conventionally been applied to the analysis of brain tissue motion.

The disclosed subject matter includes inexpensive, convenient, and effective methods of evaluating and monitoring the progress of patients in acute stroke, intensive care, and emergency medicine, etc.

One proposed technique would be used as a frontline investigative tool to monitor development of brain injury and responses to treatment in the crucial hours following brain trauma or stroke One hypothesis states that the sum of the intracranial volumes of blood, brain, CSF, and other components (for example, tumor, hematoma) is constant. The skull is considered as an enclosed and inelastic container. An increase in the volume of any one of the intracranial contents is typically offset by a decrease in one or more of the others, or is associated with a rise in ICP. Intracranial blood (especially in the venous compartment) and CSF are the two components whose volume can adapt most easily to accommodate an increase in the volume of intracranial contents.

According to an aspect of the disclosed subject matter, certain methods and kits and apparatus are provided that allow a standardized procedure in which normal brain motions and pulsations restricted by brain swelling can be determined and/or monitored in various conditions, regardless of operator ability or input.

According to another aspect of the disclosed subject matter, a kit for predicting intracranial pressure increase in a patient can include an ultrasound sensor and elastic band for attaching the sensor to a patient's head and a communication system (wire or wireless) for communicating information from the ultrasound sensor to a controller.

According to another aspect of the disclosed subject matter, a method of determining brain swelling in a patient, can include placing an ultrasound transducer adjacent the brain of the patient, determining at least one of location and motion of a first tissue portion relative to a second tissue portion based on information received by the transducer, and providing an intracranial pressure increase alarm when an increase above a target amount in the motion of the first tissue portion relative to the second tissue portion is determined.

According to another aspect of the disclosed subject matter, a method of determining brain swelling in a patient, can include calculating displacement of brain tissue utilizing the following formula:

$$\text{displacement}'(t) = \text{theta}'(t) * \text{lambda}/2/2\text{pi} - \text{theta}'(t0) * \text{lambda}/2/2\text{pi}; \text{ and}$$

$$\text{theta}'(t) \square \arg(IQ\text{data}(t) - IQ \text{ centerpoint}),$$

where:
displacement'(t) is tissue displacement (swelling/shifting) from IQ center point;
theta'(t) is IQplot argument (IQ phase angle) from IQ centerpoint;
IQdata(t) is IQ data at time t; and IQ centerpoint is IQ trajectory center point.

According to another aspect of the disclosed subject matter, an apparatus for determining brain swelling in a patient can include, an ultrasound transducer, an attachment structure configured to attach the transducer to the patient for continuous monitoring of the brain, and a controller configured to calculate displacement of brain tissue based on information from the ultrasound transducer, the controller configured to remove data sensed by the ultrasound transducer due to at least one of a cardiac cycle and a respiratory cycle of the patient.

According to another aspect of the disclosed subject matter, an apparatus for determining brain swelling can include a controller configured to calculate displacement of brain tissue utilizing the following formula:

$$displacement'(t)=theta'(t)*lambda/2/2pi-theta'(t0)*lambda/2/2pi; \text{ and}$$

$$theta'(t)=arg(IQdata(t)-IQ \text{ centerpoint}),$$

where: displacement'(t) is tissue displacement (swelling/shifting) from IQ center point, theta'(t) is IQplot argument (IQ phase angle) from IQ centerpoint; IQdata(t) is IQ data at time t, and IQ centerpoint is IQ trajectory center point.

Although the apparatus and method are effective in predicting intracranial pressure increase due to brain swelling, the method can also be effective in predicting other increases in pressure such as due to compartment syndrome of muscles in the legs or arms, which is similar in most respects (a limited containing volume, enclosing expanding tissue or fluid space which results in the loss of blood supply (ischemia) and tissue death).

BRIEF DESCRIPTION OF THE DRAWINGS

The disclosed subject matter of the present application will now be described in more detail with reference to exemplary embodiments of the apparatus, kits and method, given by way of example, and with reference to the accompanying drawings, in which.

DETAILED DESCRIPTION OF EXEMPLARY EMBODIMENTS

Figure 1A:
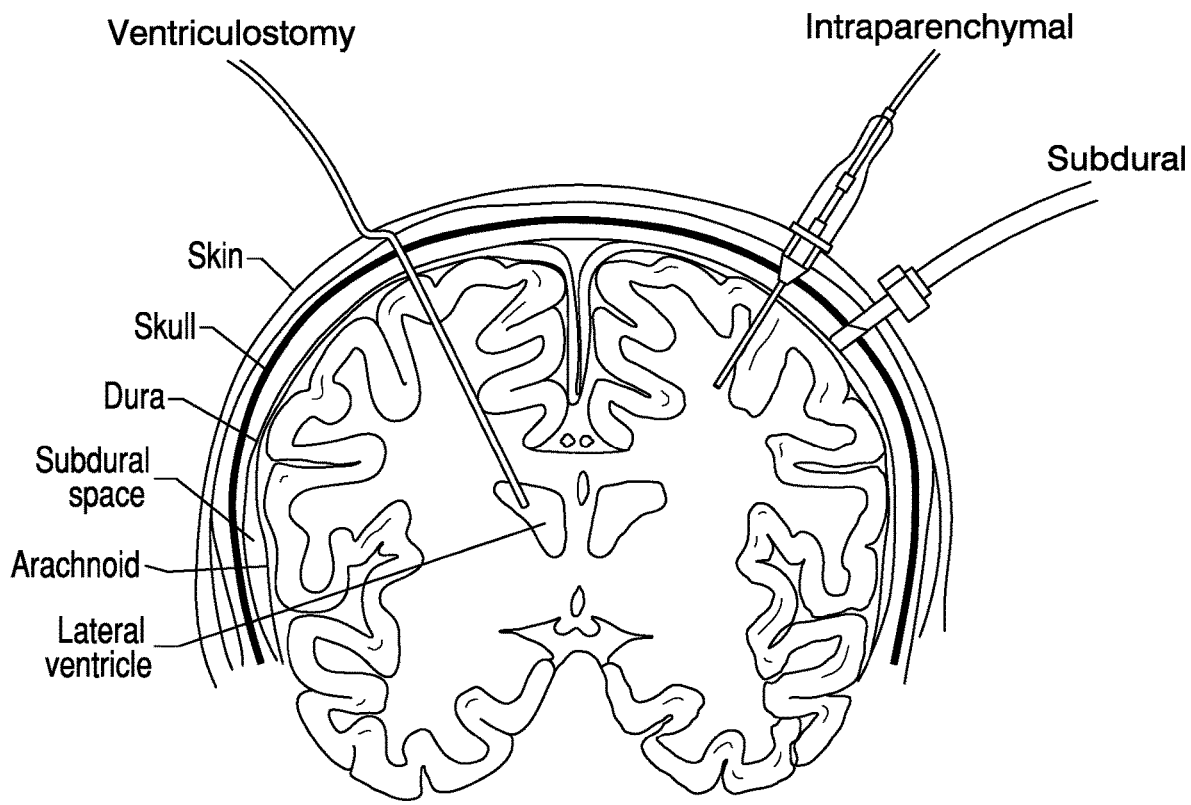
FIGS. 1A and 1B are a cross section of a patient depicting conventional ICP monitoring and a conventional ICP measurement probe, respectively.
Figure 1B:
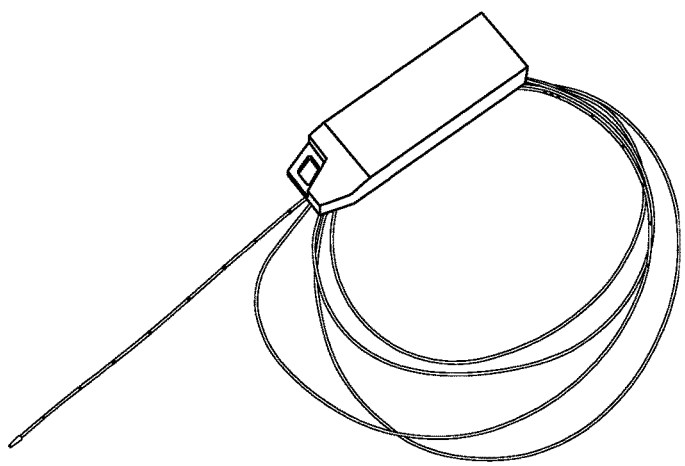
Figure 2:
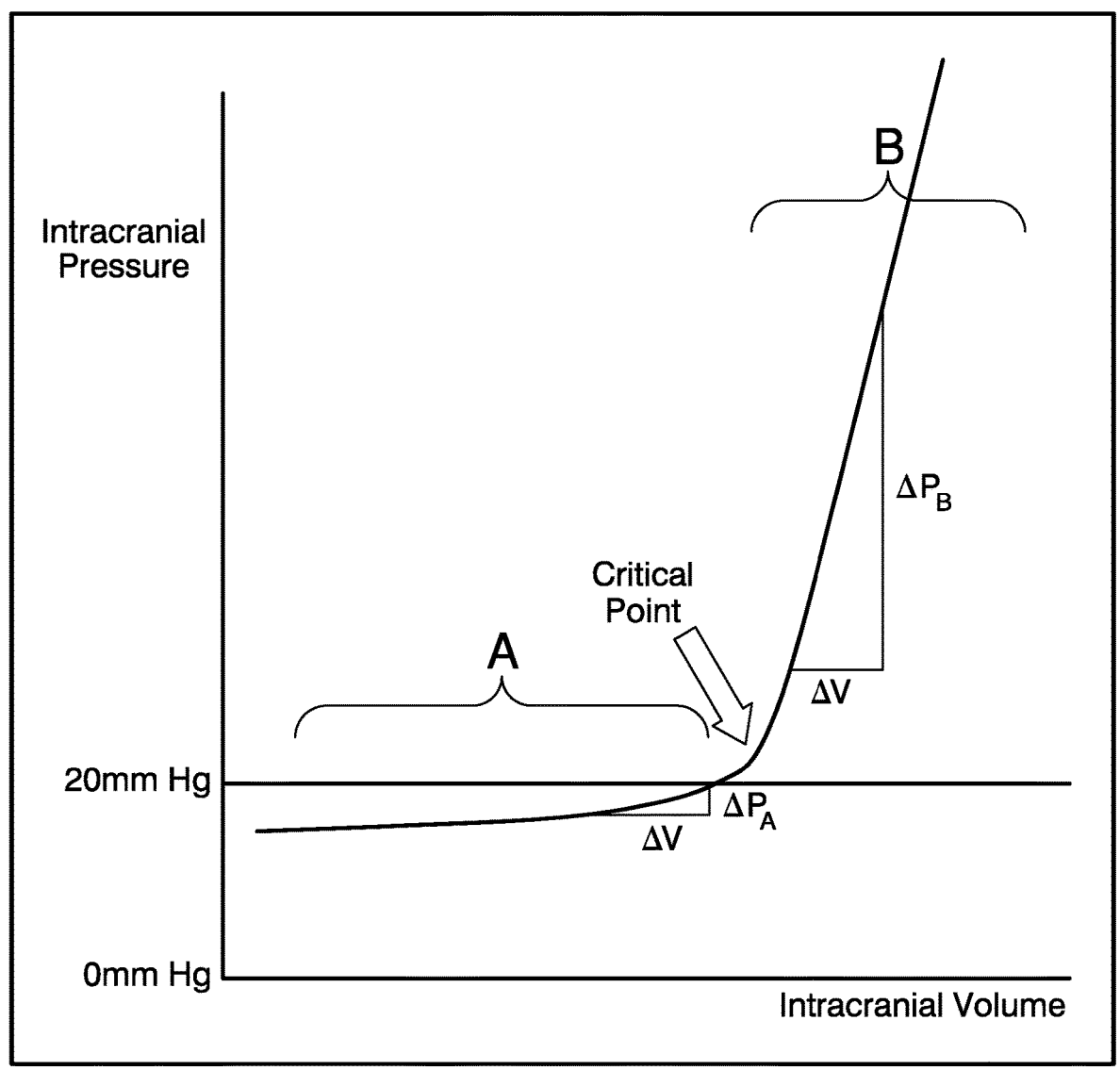
FIG. 2 is an intracranial pressure-volume curve.

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

1. Exemplary Method and Apparatus for Determining Brain Swelling and/or Predicting Increase in Intracranial Pressure The cranial braincase is a fixed volume containing "semi-solid" neurological tissue and other solids plus liquid blood and cerebral-spinal fluid. The only major outlet is the foramen magnum containing the brainstem including channels for CSF flow to and from the ventricles to the spinal cord. Blood vessels provide additional communications between the calvarium and the exterior. The current standard of practice for assessing intracranial pathology includes the measurement of Intra-Cranial Pressure (ICP). Intracranial pressure can be reviewed in various time increments, such as seconds (C waves), minutes (B waves), fractions of hours (A waves), or on a daily basis, to provide information about the likely outcome of the case and to provide information necessary for treatment. ICP is measured in various types of cases, such as stroke, osmotic metabolic disease, unexplained coma, hydrocephalus, and head trauma. Some publications suggest that ICP measurement would be useful in the evaluation of severe headache, gait disturbances, incontinence and dementia.

In the case of head trauma, the time course of ICP can be correlated with patient outcome. For example, in cases considered to have an "early profile" where ICP was elevated for two days or less, the patient outcome was relatively good. In cases considered to have an "intermediate profile" where ICP was elevated for a time period between two and five days, the patient outcome was not as good as in early profile cases. In cases considered to have a "late profile" where ICP was elevated greater than five days, the patient outcome was more often severe, including vegetative state and death. In addition, if a mass were removed from the brain or skull during treatment, the number of intermediate profile cases dropped from 40% to 12%, while the early and late profile cases increased from 25% to 40% and from 35% to 50%, respectively. Thus, patient outcome was related to the ICP profile: good outcome was rare in "late profile" cases compared to "early profile." Death, persistent vegetative state and severe disability were higher in "late profile" cases compared to "early profile" cases.

The cause of the poor outcome correlation with long duration High ICP might be due to brain tissue ischemia due to low Cerebral Perfusion Pressure (CPP), the difference between Blood Pressure (BP) and ICP.

CPP=BP−ICP

CPP is similar to transmural pressure (BP—tissue pressure) that sustains inflation of arteries and veins. Transmural pressure is related to muscle compartment syndrome, in which elevated tissue pressure due to edema within a confined fascial compartment compresses the patency of veins and arteries. Because the vascular walls are flaccid, the lumen collapses as the tissue pressure exceeds the luminal pressure.

CPP analysis considers the contents of the cranium to be liquid with isotropic, uniform pressure distribution, a simplification that might obscure a better understanding. Thus the ICP measurement from a single point might not be sufficient to characterize the pressure throughout the volume of the cerebrum and cerebellum because the major content of the cranium is semi-solid, tethered at multiple locations, and divided by fascia into compartments.

As a mass or swelling expands in a portion of the brain, the solid tissue will distort and deflect the boundaries creating differing regions of pressure within the cranium. In addition, tethering will create further alterations in pressure. One example of tethering is the Superior Sagital Sinus, which has a negative transmural pressure, but is stretched open by the tether of the Falx Cerebri. Of course, in solid tissue, pressure is not isotropic (equal in all directions). The differences in pressure in different regions of the brain will cause the arterial, arteriolar, venular and venous transmural pressure to differ between regions. Low transmural pressure in one region might decrease or obstruct perfusion in that region while other regions receive higher perfusion, causing the regions of decreased perfusion to become ischemic resulting in regional brain damage. In the supine patient, where venous drainage to the right atrium is via open veins and thus the respiratory variations in atrial pressure are reflected in the cerebral venules, an increase in pressure in a portion of the brain will result in adverse venular transmural pressure and a decrease in the respiratory tissue volume changes. This condition will also result in an increase in arteriolar pulse amplitude, as the "cushioning effect" of the venules is lost. In a patient with more severe regional cerebral pressure increases, the arteriolar transmural pressure might become unfavorable leading to a loss of brain perfusion indicated by the loss of the tissue arteriolar pulsations. Applicant notes that if the ICP exceeds the arterial pressure, especially exceeds the systolic brain arterial pressure (arm blood pressure (=120 mmHg)−Elevation hemostatic decrease (=30 mmHg~40 cmElevation)=90 mmHg, then the brain strain pulse amplitude should decrease to zero, when the ICP is between diastolic and systolic pressure, then the pulsatile strain should be large.

There is also a possibility of regional perfusion that could be monitored or predicted in accordance with the presently disclosed subject. Because the pressure is likely to be different in different compartments of the cranium, a region of increased pressure might have depressed perfusion compared to another.

In addition, it is possible that "slow waves" exist that can be measured on the order of a minute or so, that are due to major shifts of tissue, releasing "bottled up" pressure, that are likely similar to "earthquakes" that will cause large brain motions. Certain noise filters can be incorporated into the software and/or hardware of the disclosed subject matter in order to protect data from being swamped or somehow made less effective by these "earthquake" type of events.

In pathological cases, ICP increases by various mechanisms, including for example: 1) the obstruction of the outflow of Cerebral Spinal Fluid (CSF) leading to hydrocephalus; 2) the expansion of solid tissue including: 2a) brain edema, 2b) intracranial hematoma, and 2c) tumor.

Some in-vivo models of ICP have measured "brain elasticity" (dP/dV) by the infusion of fluid into brains or spinal cords, assuming that the brain tissue is compressible or that the vascular and fluid spaces in the cranium have elastic boundaries. Here we consider an alternate conception of the cranio/cerebral dynamics.

Our study investigates the potential for using Doppler ultrasound to assess brain swelling/shifting in patients with suspected stroke or head injury at bedside. Doppler ultrasound is a safe, possibly portable, continuous monitoring technique, which is already used to monitor blood flow through the major arteries, but has not so far been applied to the analysis of brain tissue motion.

The disclosed subject matter includes inexpensive, convenient, and effective methods of evaluating and monitoring the progress of patients in acute stroke, intensive care, and emergency medicine.

One proposed technique would be used as a frontline investigative tool to monitor development of brain injury and responses to treatment in the crucial hours following brain trauma or stroke.

Figure 3:
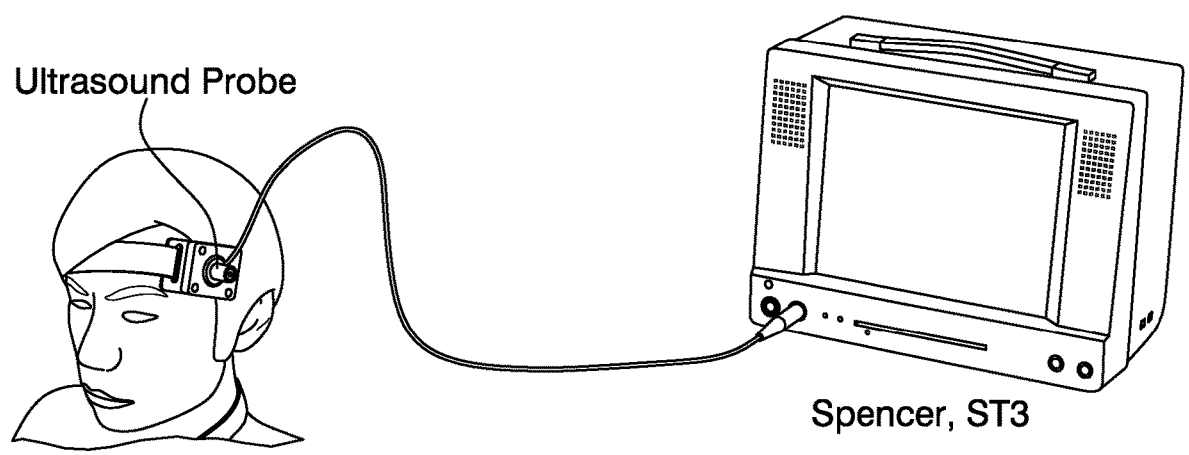
FIG. 3 is a perspective view of an embodiment of the presently disclosed subject matter.
Figure 4:
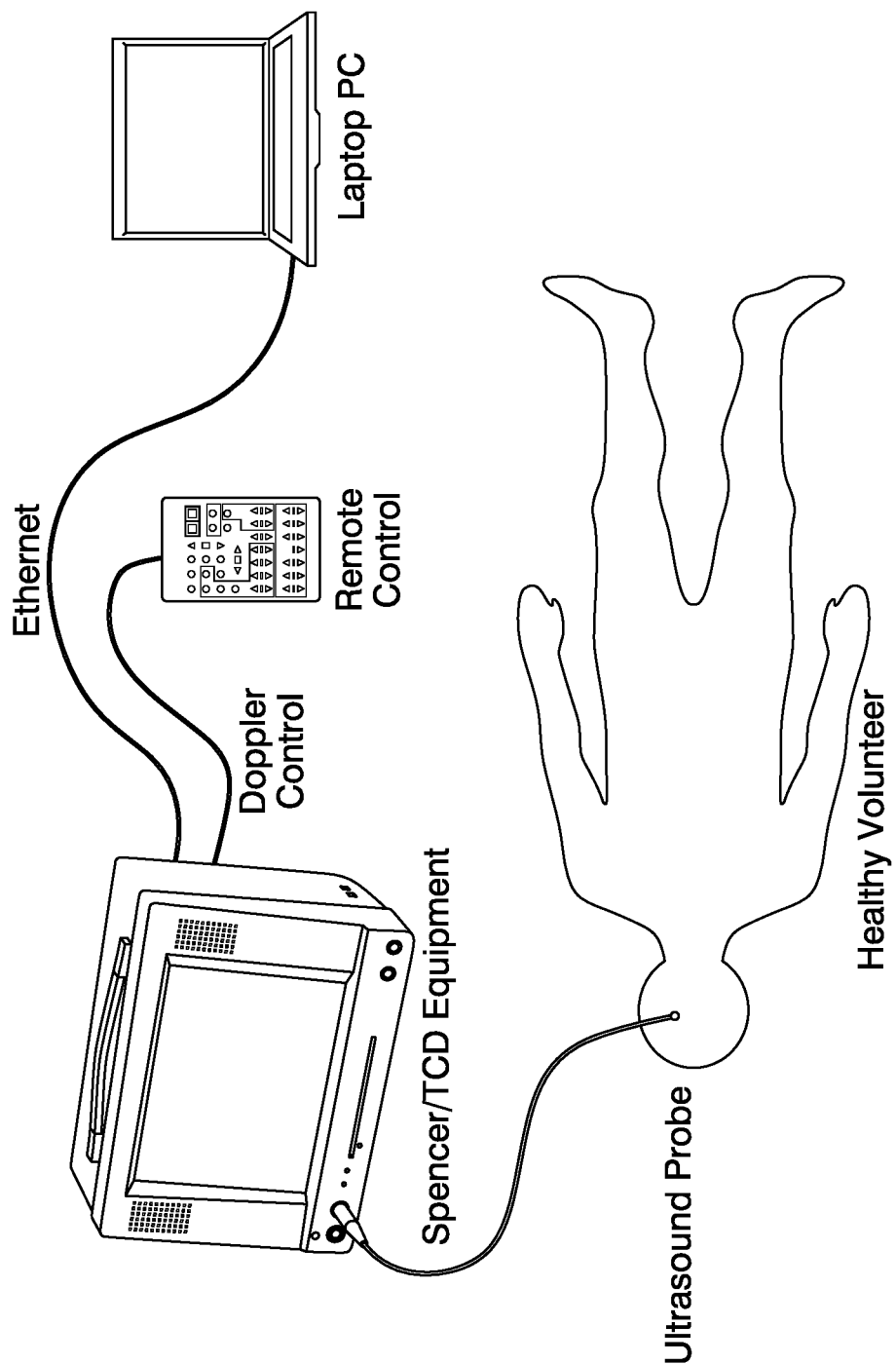
FIG. 4 is a schematic view of an embodiment of the presently disclosed subject matter.
Figure 5:
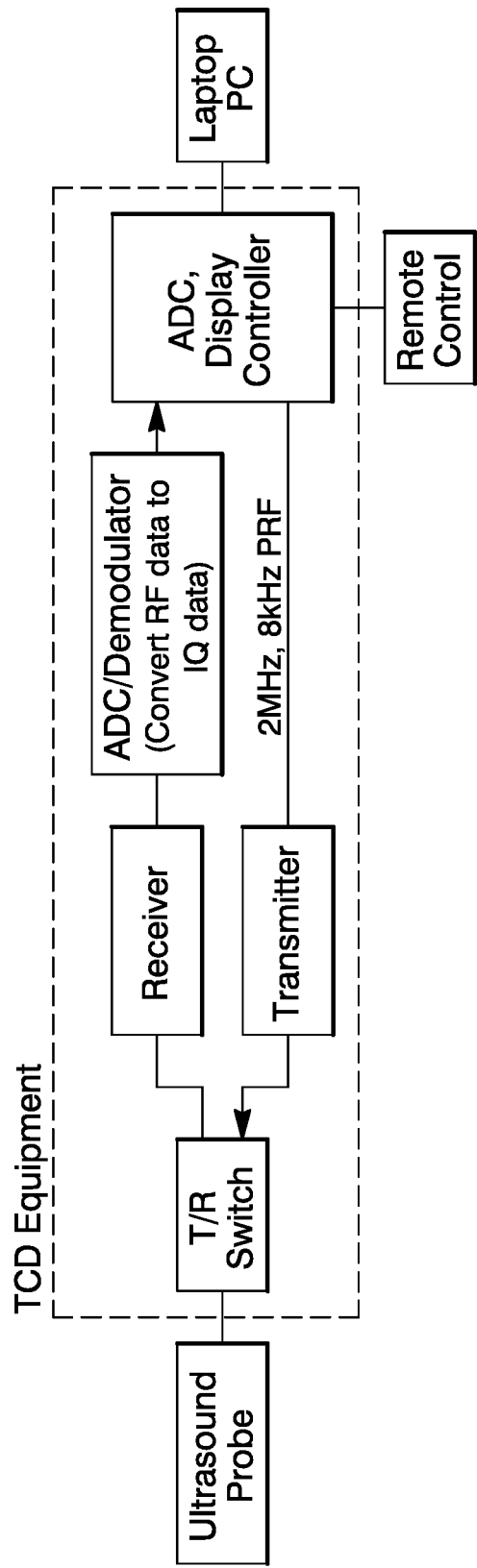
FIG. 5 is a schematic block diagram showing an embodiment of the presently disclosed subject matter.

In accordance with one embodiment of the disclosed subject matter, system and measurement algorithm can be employed. As shown in FIGS. 3 and 4 an investigation test system can be employed to conduct the method of monitoring the brain of a patient. In particular, a Trans Cranial Doppler (e.g., a Spencer T3) can be used by attaching an Ultrasound probe on the temporal window or forehead using an elastic band to measure brain tissue swelling/shifting via a controller.

TABLE 1

| Doppler type | Pulse Wave Doppler |
| --- | --- |
| Ultrasound Frequency | 2 MHz |
| PRF(Pulse reputation Frequency) | 8000 KHz |
| Measuring Range (depth) | 22 mm to 87 mm |

At each depth swelling or shift of brain tissue (Displacement) from time 0 to t is calculated using the equation below.

$$\text{Displacement}(t) = \text{theta}(t)*\text{lambda}/2/2\text{pi} - \text{theta}(t0)*\text{lambda}/2/2\text{pi} \quad (1)$$

$$\text{lambda} = 1000*c/f \quad (2)$$

where;

t: time

Displacement (Gate, t): tissue displacement(swelling/shifting) um theta(t): IQplot argument (IQ phase angle)

lambda: ultrasound wavelength um c: Ultrasound speed 1.54 mm/us f: Ultrasound frequency 2 MHz The phase angle (theta (t)) is calculated from each IQ data, and the displacement is calculated by multiplying the phase angle (theta (t)) and wavelength (lambda/2). IQ data trajectory forms arcs centered at the origin of IQ plane (0,0) as shown in FIG. 6A and the tissue displacement calculated by equation (1) is shown in FIG. 6B.

This method measures brain tissue displacement from time 0 to t, but does not provide an absolute brain tissue position at a certain time. However, by using "continuous" measurement or monitoring the method can provide the total displacement from the beginning of the measurement (time 0) to current, so that it will detect if any shift or swelling of the brain tissue occurs during monitoring.

Figure 6A:
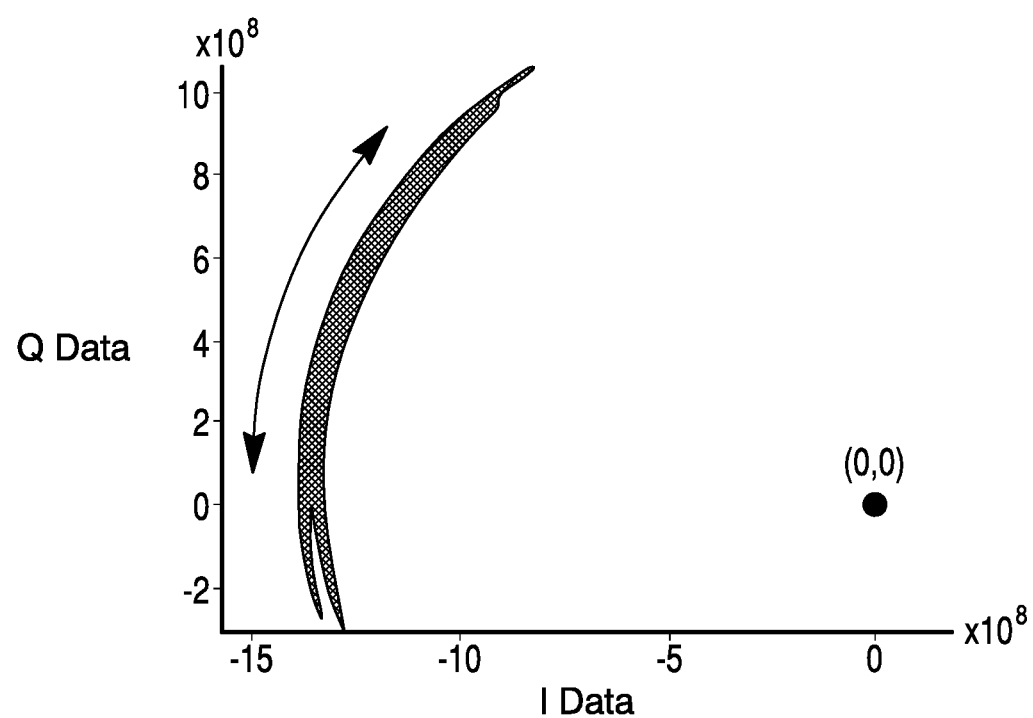
FIGS. 6A and 6B are graphs showing an example of IQ data, and tissue displacement calculated by equation (1), respectively.
Figure 6B:
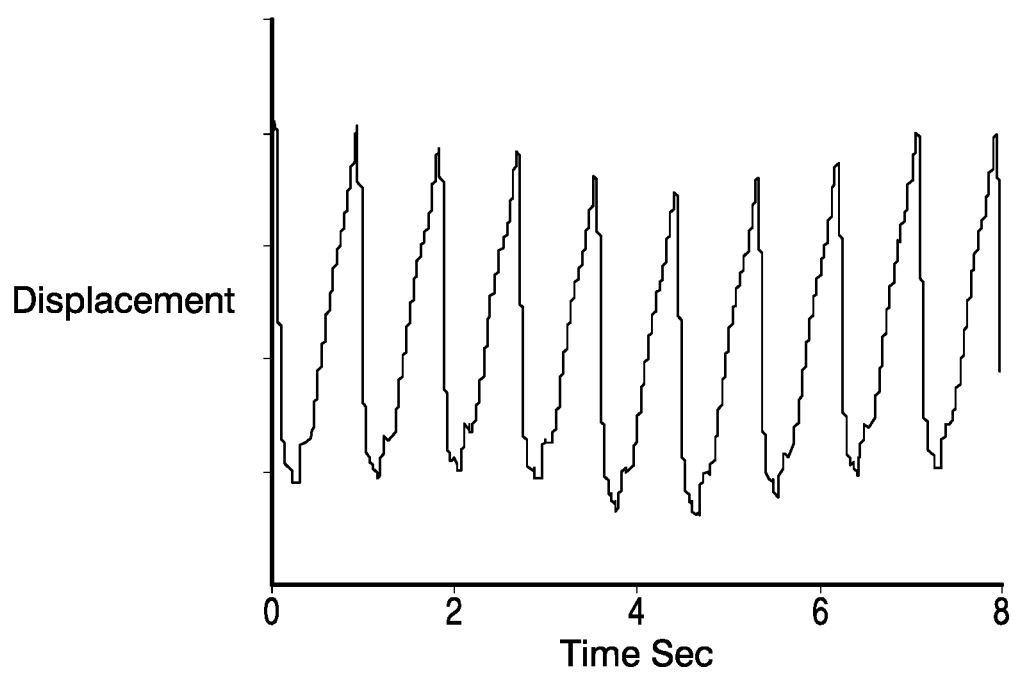

As shown in FIGS. 6A and 6B, in principle the IQ data's center point is at the origin of IQ plane (0,0), however, the IQ data often includes stationary echo clutter signal, which is caused by bone reflection and the IQ trajectory center point shifts from the origin.

Figure 7A:
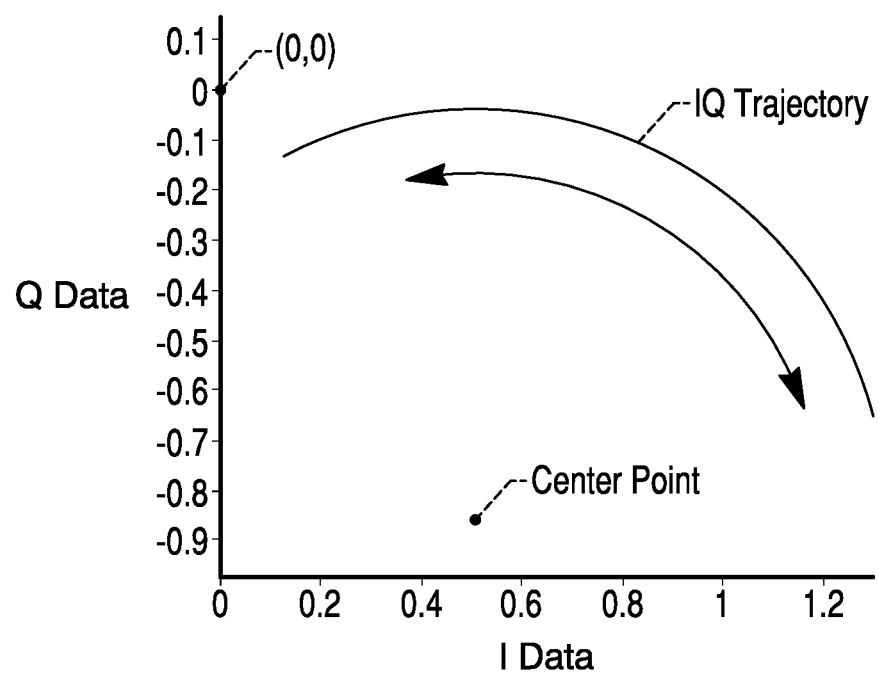
FIGS. 7A and 7B are IQ example includes stationary echo clutter signal.
Figure 7B:
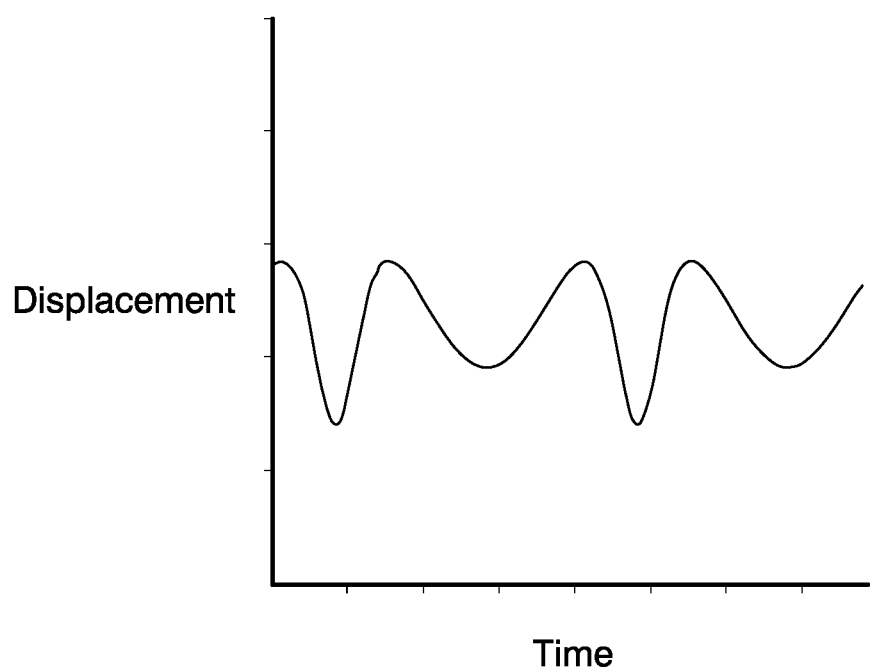

FIGS. 7A and 7B show a simulated example where IQ data includes the tissue displacement signal and stationary echo clutter signal. Sine wave can be used as a tissue displacement signal. As shown in FIG. 7A, the IQ trajectory center point is shifted from the origin, and the tissue displacement waveform calculated by equation (1) is not sine wave (FIG. 7B). Therefore, if the IQ data includes some stationary clutter signal or something that causes the shift of the center point from the origin, the equation (1) may not accurately calculate tissue displacement.

Figure 8:
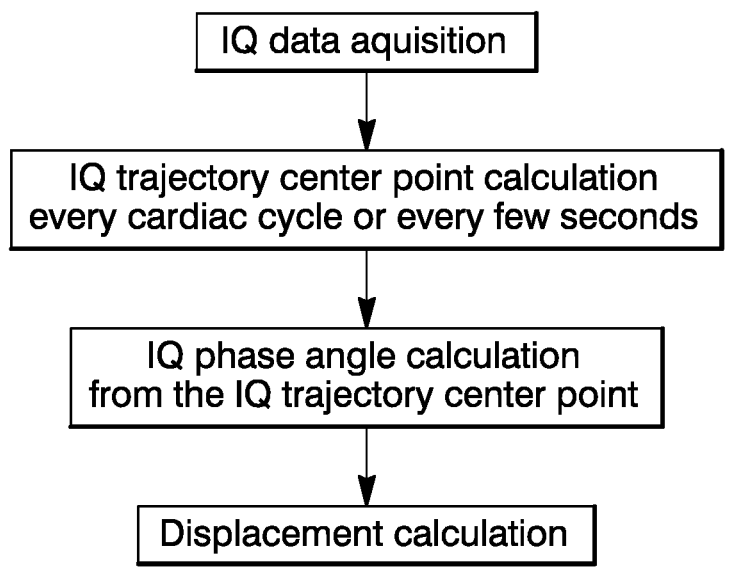
FIG. 8 is a flowchart showing an embodiment of the disclosed subject matter.

To calculate correct tissue displacement, the stationary echo clutter signal or any signals that cause the shift of the center point can be removed. When this data is removed, the IQ phase angle (IQ plot argument) is measured not from (0,0) but from an IQ trajectory center point. The IQ trajectory center point is calculated at every cardiac cycle or every few seconds, and the IQ phase angle (argument) is calculated from the IQ trajectory center point as shown in the flowchart (FIG. 8).

Figure 9A:
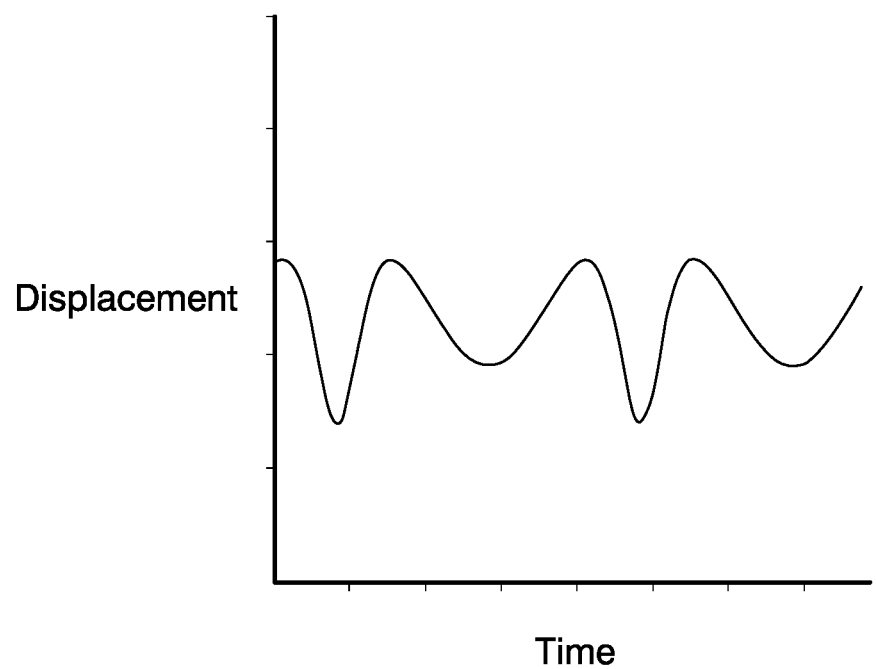
FIGS. 9A and 9B are graphs showing uncorrected and corrected displacement, respectively, representing the tissue displacement signal.
Figure 9B:
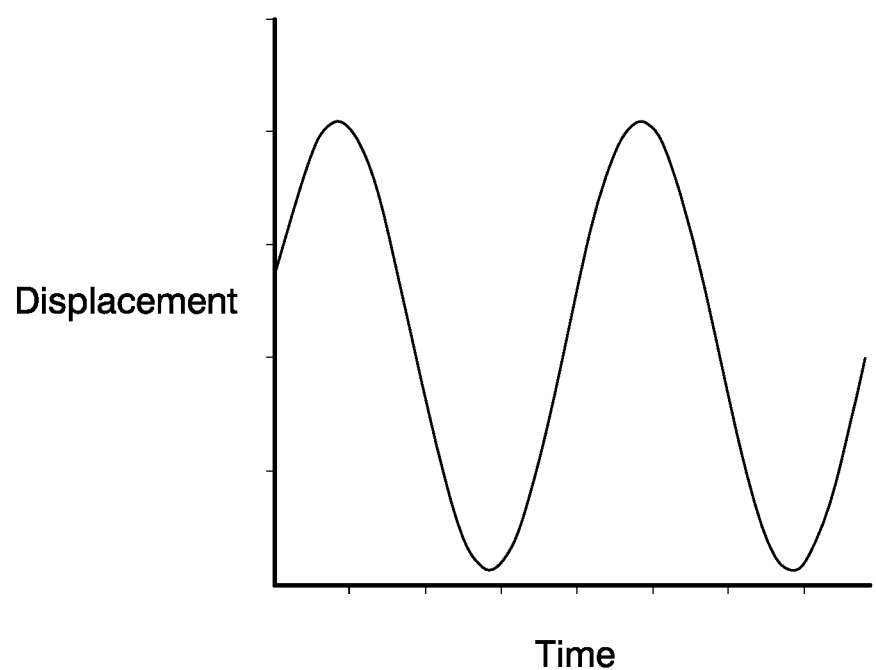

Then, the correct brain tissue displacement from time 0 to t is calculated using the equation below.

$$\text{Displacement}'(t) = \text{theta}'(t) * \text{lambda}/2/2\text{pi} - \text{theta}'(t0) * \text{lambda}/2/2\text{pi} \quad (3)$$

$$\text{theta}'(t) = \arg(IQ\text{data}(t) - IQ \text{ centerpoint}) \quad (4)$$

where;
Displacement'(t): tissue displacement (swelling/shifting) from IQ center point um
theta'(t): IQplot argument (IQ phase angle) from IQ centerpoint
IQdata(t): IQ data at time t
IQ centerpoint: IQ trajectory center point FIGS. 9A and 9B show the uncorrected displacement and the corrected displacement, which is calculated by the above equation (3). The corrected displacement (FIG. 9B) forms the sine wave that is used in the simulation to represent the tissue displacement signal. The presently disclosed algorithm is, therefore, shown to be able to remove the stationary echo clutter signal.

Brain motions attributed to heart and breathing cycles can be removed using the above algorithm to calculate brain position and thus, true swelling can be clearly discernable with the presently disclosed device and method. Moreover, the cyclical displacement of brain tissue due to heart cycle and variation in blood pressure and/or concurrent breathing can be removed from the measurement method and the device and method can provide accurate brain position and movement data through the use of a Doppler type ultrasound sensor and controller.

Safety guidelines for transcranial Doppler monitoring issued by the British Medical Ultrasound Society are typically followed at all times (BMUS 2009). These state that:

TABLE 2

| | | TIC | | |
|---|---|---|---|---|
| | Values to | Thermal index value | | Mechanical index value |
| Application | monitor | 0-1.0 | >1.0 | 0-0.3 >0.7 |
| Adult transcranial (imaging and stand-alone) | TIC and MI | ✓ | Restrict time to:<br>0.7 < TIC ≤ 1.0: 60 min<br>1.0 < TIC ≤ 1.5: 30 min<br>1.5 < TIC ≤ 2.0: 15 min<br>2.0 < TIC ≤ 2.5: 4 min<br>2.5 < TIC ≤ 3.0: 1 min<br>TIC>3: not recommended | ✓ Risk of cavitation with contrast agents |

TIC—thermal index for cranial bone,
MI—mechanical index

Therefore, it was decided to record measurements using a power (TCD system power) of 40% to maintain a TIC of <1.0.

Healthy volunteer test
To validate the assumption, we did the following testing.
Valsalva maneuver test
supine posture (−20 deg) test.
Valsalva maneuver
The Valsalva maneuver is performed by moderately forceful attempted exhalation against a closed airway, usually done by having a patient close their mouth, pinching the patient's nose shut, while having the patient exhale or press out as if blowing up a balloon.

During Valsalva maneuver testing, the intrathoracic pressure increases, and central venous pressure also increases. Accordingly, the venous blood volume in brain typically increases and, as a result, the brain swells. (ICP would also increase.) Therefore, we expect that the brain swelling can be measured using the ultrasound transducer attached on the head during Valsalva maneuver testing.

The valsalva maneuver test protocol is as follows;
Probe position: Temporal window
Protocol:
Rest: about 10 second
Valsalva maneuver: about 30 second
Rest: about 30 second
Supine(−20 deg) posture test
During supine posture, the venous intracranial venous blood volume in brain would increase and accordingly, the brain tissue would also swell. We expect that the brain swelling can be measured using an ultrasound sensor when the patient is in the supine posture.

The Supine(−20 deg) posture test protocol is as follows;
Probe position: Temporal window
Protocol:
sitting: about 20 second
Supine (−20 deg): about 60 second sitting: about 40 second
Result
Valsalva Maneuver FIG. 6-8 show the brain tissue data during Valsalva maneuver. The measurement depth from head surface is 25 mm, 50 mm and 75 mm respectively.

Figure 10:
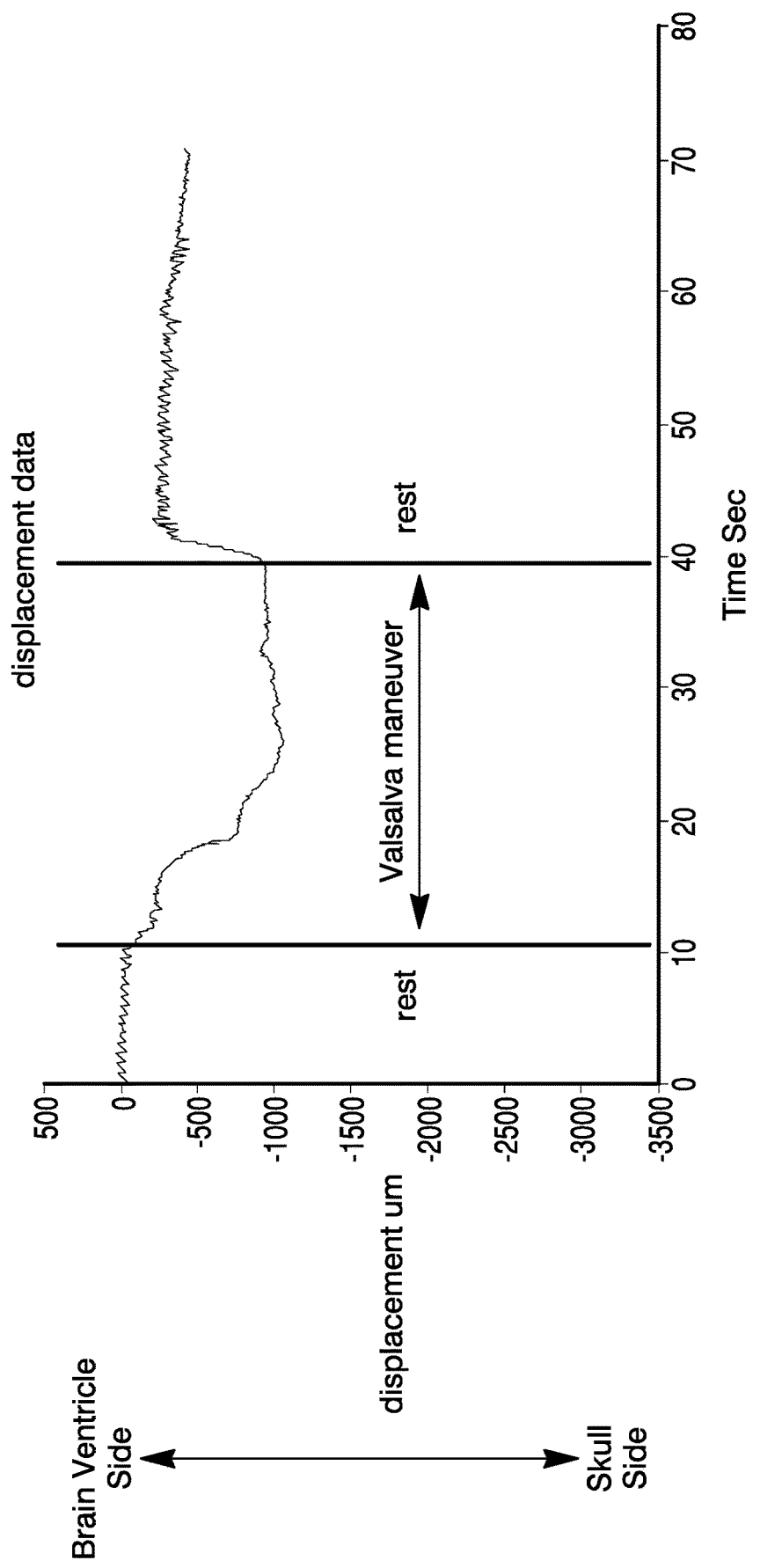
FIG. 10 is a graph showing brain tissue displacement (depth 25 mm).
Figure 11:
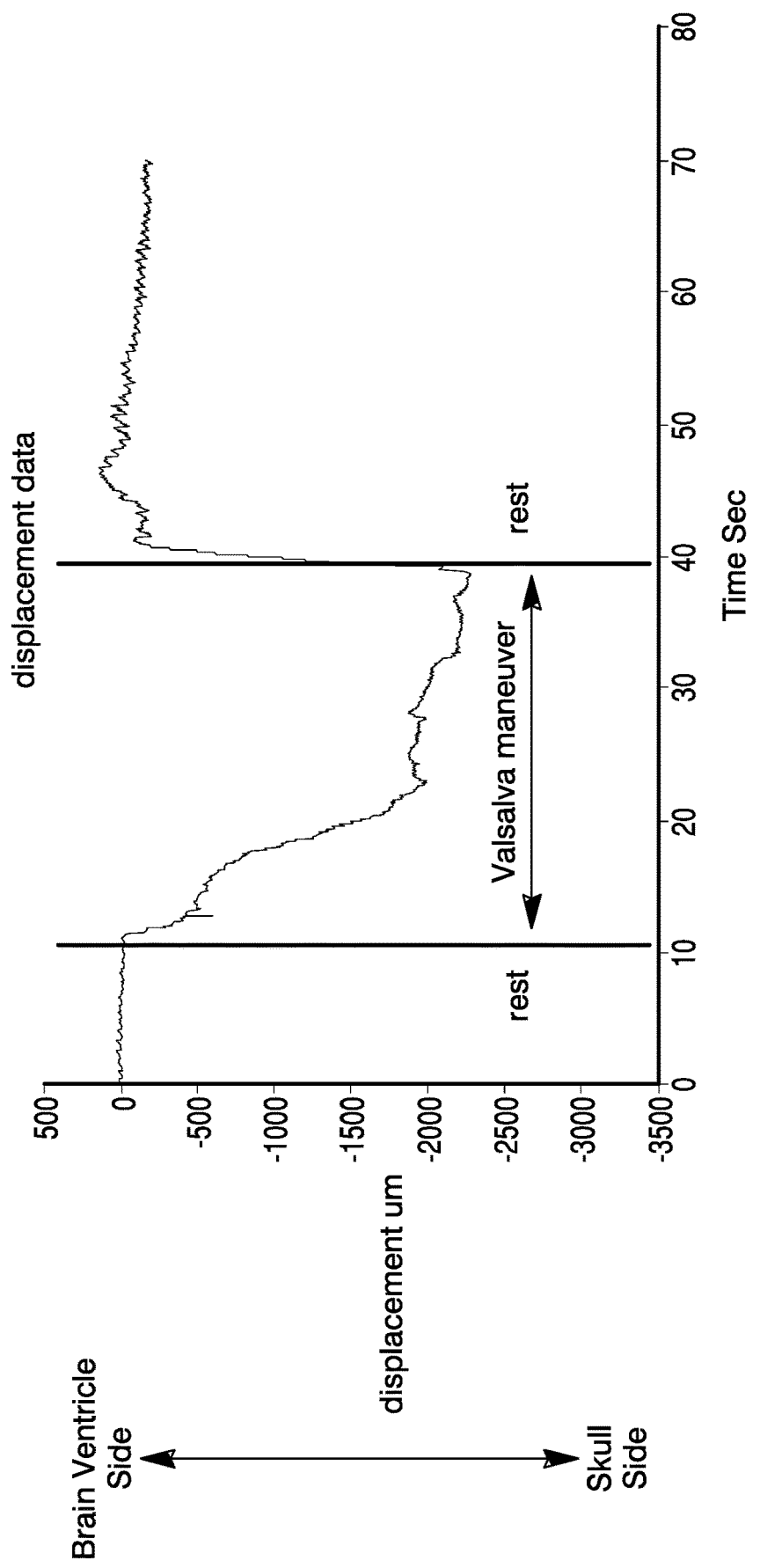
FIG. 11 is a graph showing brain tissue displacement (depth 50 mm).
Figure 12:
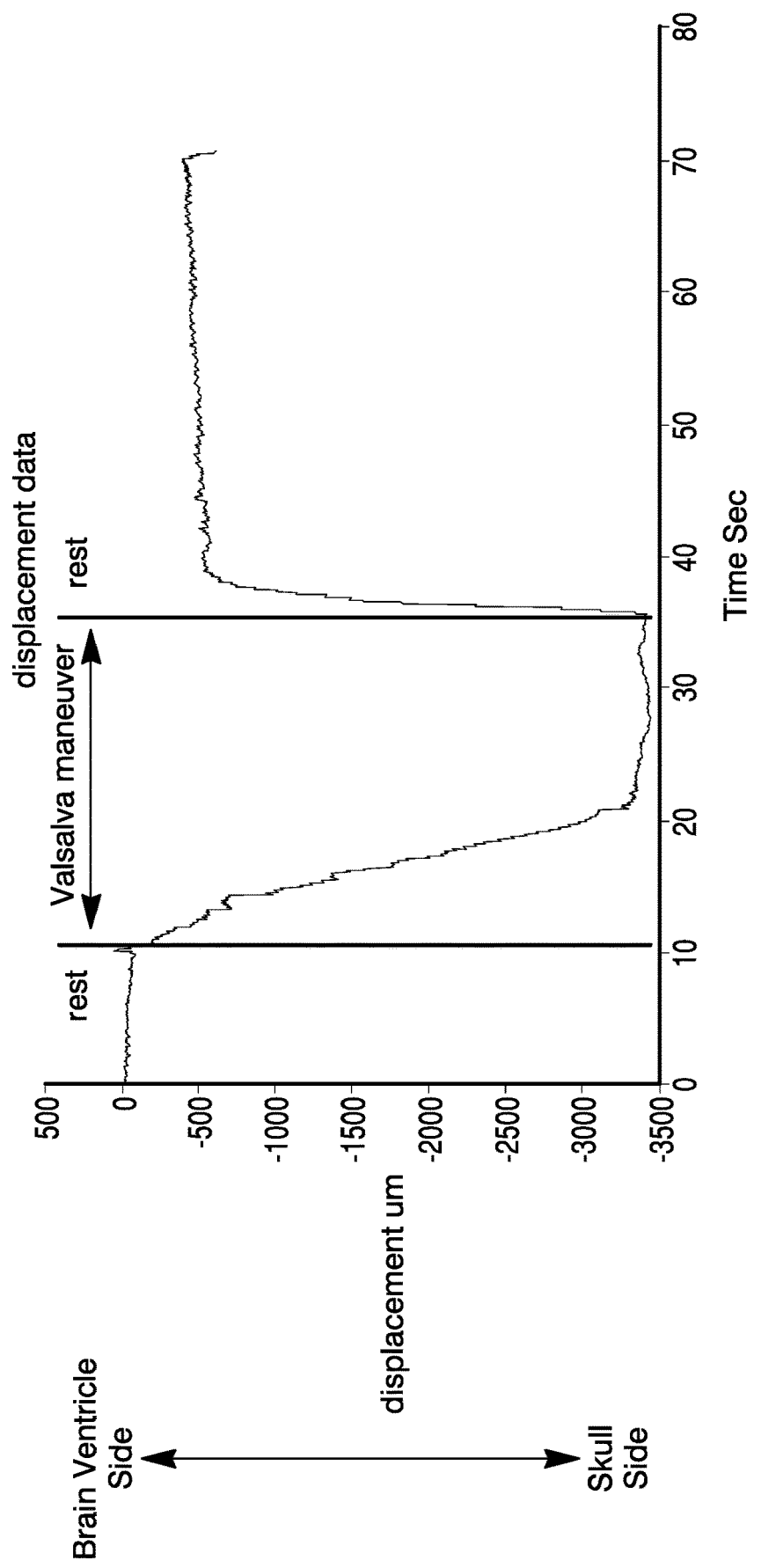
FIG. 12 is a graph showing brain tissue displacement (depth 75 mm).

As shown in FIGS. 10-12, the ultrasound system could measure brain tissue displacement and this means "brain swelling measurement". In the 25 mm depth measurement, the brain tissue swelled around 1.0 mm. In the 50 mm depth measurement, the tissue swelled 2.5 mm, and in the depth 75 mm, the displacement was around 3.5 mm. Therefore deeper brain tissue swelled more. The reason is that, because the brain tissue is enclosed in rigid skull and the brain tissue is like a "sponge", we think the deeper brain tissue can swell more.

Supine(−20 deg) posture

Figure 13:
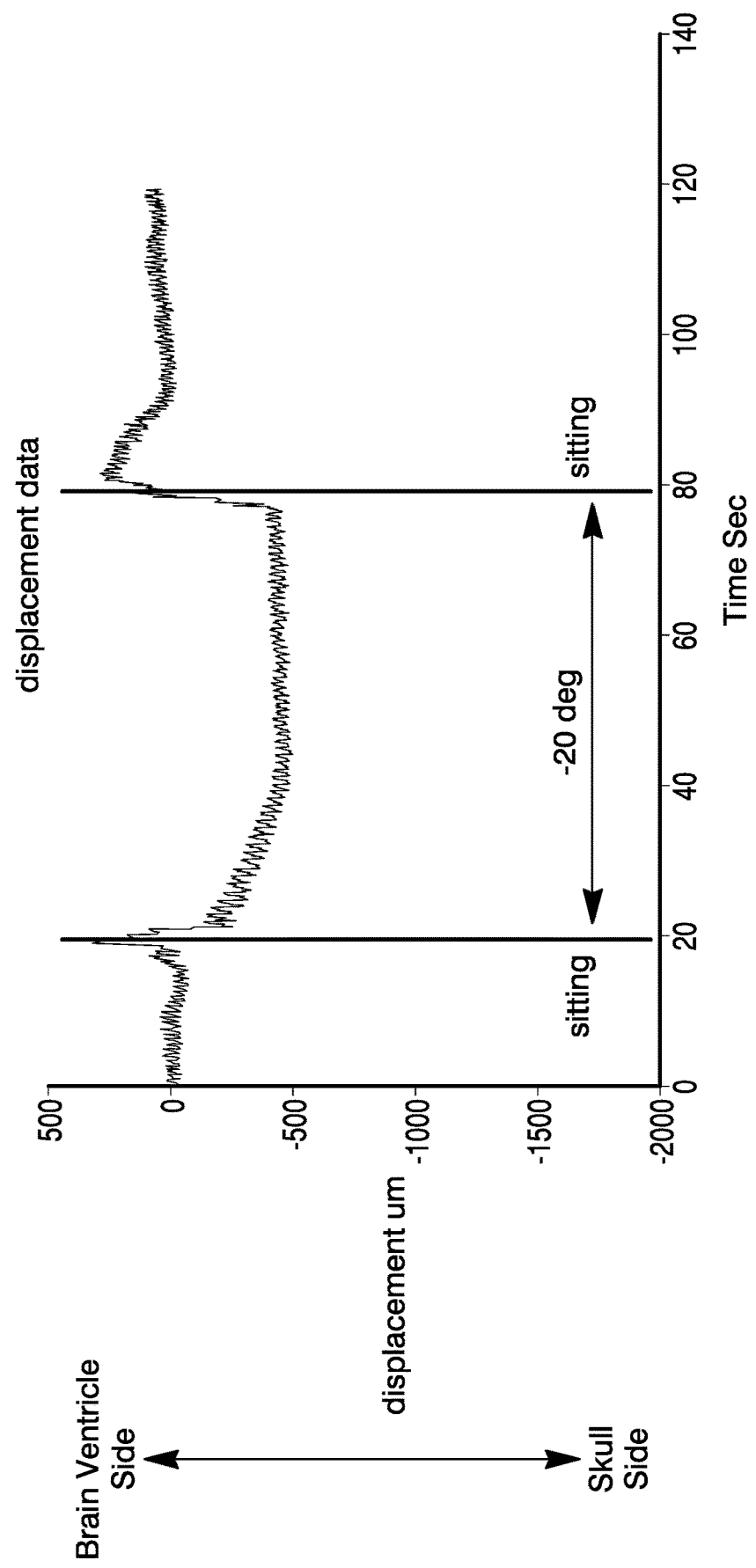
FIG. 13 is a graph showing brain tissue displacement (depth 25 mm) when patient is in supine position.
Figure 14:
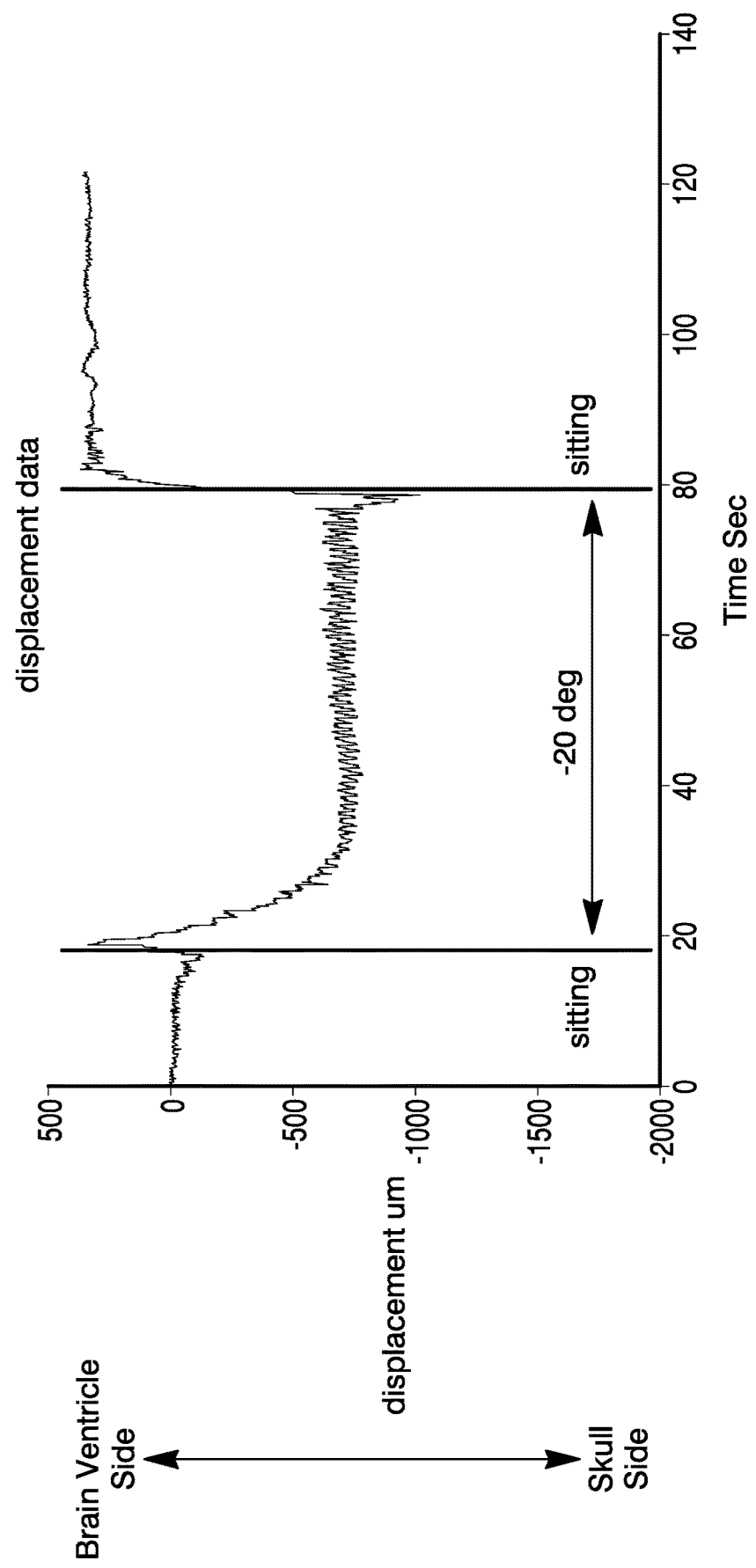
FIG. 14 is a graph showing brain tissue displacement (depth 50 mm) when patient is in supine position.
Figure 15:
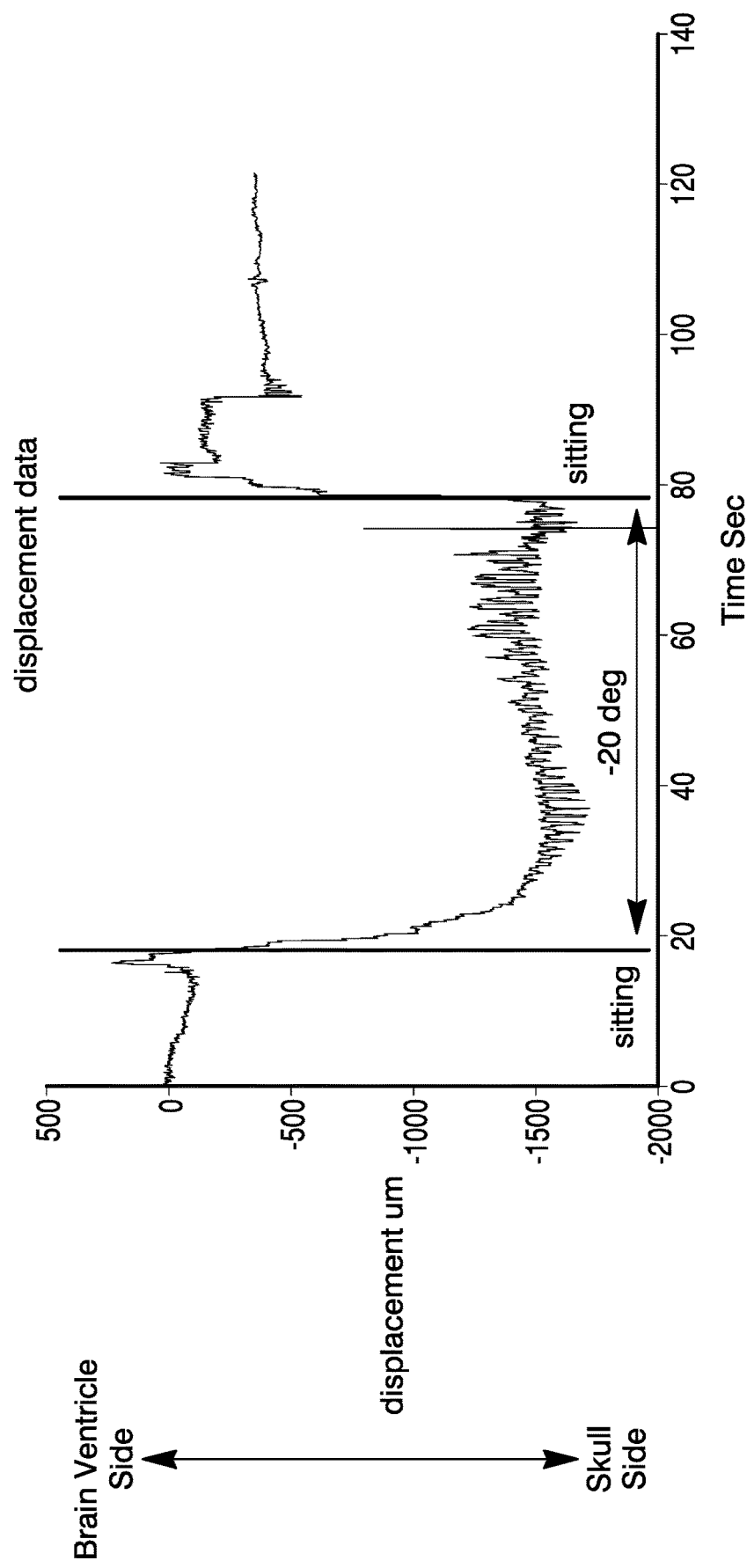
FIG. 15 is a graph showing brain tissue displacement (depth 75 mm) when patient is in supine position.

FIGS. 13-15 show the brain tissue data during Valsalva maneuver. The measurement depth from head surface is 25 mm, 50 mm and 75 mm respectively.

As shown in FIGS. 13-15, brain tissue displacement could also be measured in supine posture testing using the ultrasound system. In the 25 mm depth measurement, the brain tissue swelled around 0.5 mm. In the 50 mm depth measurement, the tissue swelled 0.75 mm, and in the depth 75 mm, the displacement was around 1.5 mm. The deeper brain tissue swelled more, and this is similar behavior to Valsalva maneuver testing.

Brain swelling can be measured using ultrasound. This brain swelling/shifting monitor can be a new tool to avoid second brain injury. An EKG-electrode-like ultrasound transducer and connected to a patient as shown in FIG. 3 would make continuous measuring and monitoring easier to use and facilitate measurement of brain swelling. The disclosed swelling monitor can be used as new patient monitor parameter. The disclosed swelling monitor and method for use can measure swelling/shifting and also measure the progress of swelling going down.

Features of the swelling monitor and method for use include brain swelling/shifting monitor using ultrasound, continuous monitoring at a patient's bedside, and measurement of "relative" brain tissue displacement. Therefore, according to one embodiment of the device and method of the disclosed subject matter, measurement is continuous, and not in an intermittent measurement manner.

It should be noted that the ultrasound transducers can be "communicatively connected" to a controller by a hard wire connection (such as metal wire, fiber optics, or other hard connection) or by a wireless connection (such as wi-fi, bluetooth technologies, and other radio-frequency connections or other wireless communication protocols). In operation, the controller can be integrated into or separate from a typical ultrasound device, and includes software and or hardware configured to obtain, determine and/or monitor the location of a first brain tissue portion relative to a second brain tissue portion. The software and/or hardware can be configured such that positional information of a first target tissue is obtained and then compared to positional information related to a second target tissue. If the information indicates an expected pulsation over time with the cardiac cycle, then the controller will determine that the brain is free to expand normally. If the information indicates a periodic expansion with respiration, then the controller will determine that the venous pressure in brain exceeds the intracranial pressure, which is normal in a supine patient. If the information indicates a change of position over time in concert with an accelerometer monitoring skull position and/or orientation, then the controller will determine that the brain is folating normally in the CSF. If the information indicates a progressive change over time, then the controller will determine that the brain is swelling. If the information indicates either a decrease in change over time, or indicated no relative movement after a period of movement, then the controller will determine that the brain is swelling and that ICP will increase in the near future. Upon the controller determining that ICP will increase, information can be provided to a practitioner via a monitor or via a remote alarm device such that the practitioner will be informed that ICP will likely increase in the patient. The monitor device can be built into or attached to the controller either via a wired or wireless connection. Similarly, the alarm device can be attached to the controller either via a wired or wireless connection. Alternatively, the alarm device can be a cell phone or other type of remote communication device. The controller can also be configured to provide information to a server that then manages the information and communicates to various recipients (such as alarm device in the form of a cellular phone, tablet, computer, etc.). Various applications can also be developed to best manage and deliver the information to specific remote devices.

It should be noted that radio frequency phase demodulation can be used in the disclosed subject matter to obtain the desired resolution from the ultrasound (or other) transducer. For example, resolution can be such that $1/10$ micron displacements can be measured within the brain tissue.

The controller can also be connected to other sensors to provide for more accurate determination of positional relationships of brain tissue relative to itself (i.e., to determine the amount of change in position of a first target brain tissue relative to a second target brain tissue to determine swelling, etc.). For example, an accelerometer can be provided and attached to a patient's head and/or chest (over the sternum) to monitor position and movement of these two areas of the body such that the movement can be used to better calculate the positional relationship between the two target brain tissues or the elevation between a target brain tissue and the right atrium of the heart which is used as a pressure reference. More specifically, the accelerometers placed on the skull and sternum can be used to determine a relative elevational difference between the right atrium and the body part being measured, e.g., skull/brain. In addition, a respiratory and/or a pulmonary sensor can be attached to the controller such that respiratory and/or a pulmonary function information can be used to better calculate the positional relationship between the two target brain tissues, and to better the existence of swelling. In one example, the respiratory and/or a pulmonary sensor can be combined with either the accelerometer or the ECG sensor(s). Recently, microcircuit patches have become available that attach to a user's head like a small bandage and wirelessly transmits acceleration data for real-time monitoring of head acceleration, especially during sporting activities. It is contemplated that the accelerometer can be configured in a similar manner to include such a microcircuit. In addition, because swelling of the brain tissue is relatively small, and because there is a great deal of variability between anatomical geometry in patients, it may be helpful to use base line data to ensure greater accuracy of swelling and positional measurement and calculation. For example, base line data including skull and brain location data is sometimes collected for athletes. This type of base line information could then be utilized by the system/apparatus 1 of the disclosed subject matter to increase accuracy during use on a particular patient in which base line information is available.

Intracranial tissue, including brain tissue, exhibits natural pulsatile motions. In an upright normal person, the cardiac motion is about 20 micrometers superimposed on the respiratory motion of about 20 micrometers. The motion includes the dicrotic wave commonly found in any plethysmographic method. The presence of the dicrotic wave indicates relative vasoconstriction, and loss of this wave indicates relative vasodilation. The respiratory motion in an upright person is likely due to changes in cardiac output with respiration as the central venous pressure is less than the elevation of the head over the heart. If the person is supine, then an additional respiratory component may be present, with a different phase than the cardiac output component. The motion is bilateral, and thus the ventricles expand.

The brain (and other intracranial tissue) expands and contracts over both the cardiac and respiratory cycles. However, brain volume is constrained by the skull (and other tether points, as described above). Expansion or swelling of the brain or other intracranial tissue compresses the ventricles in the brain. Each cardiac cycle causes the brain to move medially, posteriorly, and caudally. These motions are the basis of the monitoring system proposed for determining intracranial tissue swelling, which is the cause of increased intracranial pressure in most cases.

Figure 16:
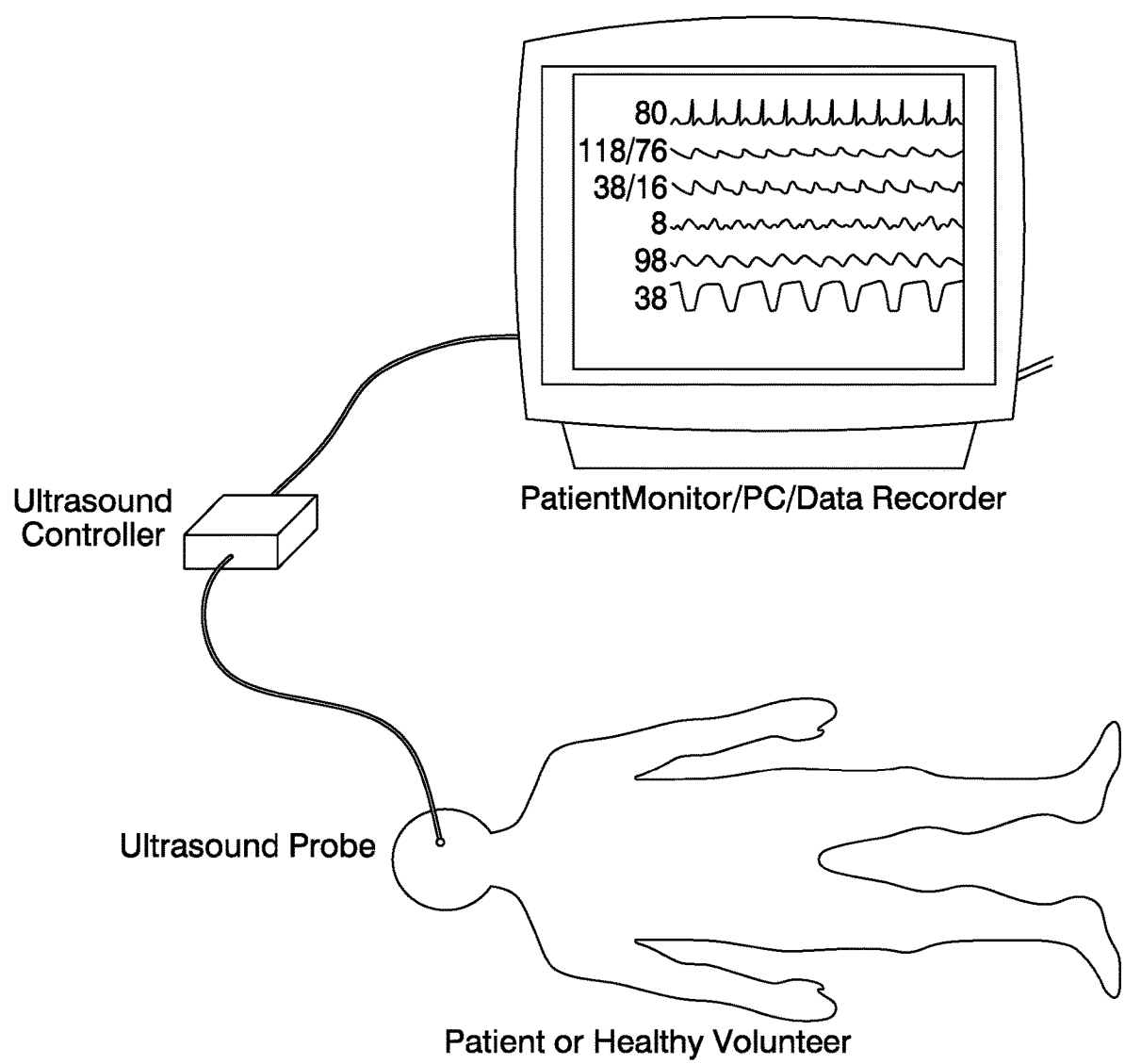
FIG. 16 is a schematic view of another embodiment of the presently disclosed subject matter.

FIG. 16 is a schematic view of another embodiment of the presently disclosed subject matter. In this embodiment, a brain tissue swelling/shifting monitor is connected via an ultrasound probe or transducer to a patient or other user. The ultrasound probe can be attached to the patient's head by a flexible band that directs the probe at certain target areas. The ultrasound controller connected to the ultrasound probe transmits bursts of high voltage pulses to the probe, and accordingly the probe generates ultrasound waves. The probe then receives the ultrasound signal (RF signal), reflected from patient's brain tissue (as well as other tissue surrounding the brain). The controller calculates the brain tissue displacement from IQ data that is generated from the ultrasound RF signal. The tissue displacement data can be sent to a recording/monitoring device such as a patient monitor, computer, or other data control or storage device or a networked system. The controller can be built into or attached to the patient monitor (or other data recorder) either via a wired or wireless connection. For example, the controller can be built into monitoring devices associated with a central monitoring system, such as those disclosed in U.S. Pat. No. 8,638,192, or into bedside monitor devices such as those disclosed in U.S. Pat. No. 9,049,993.

Figure 17A:
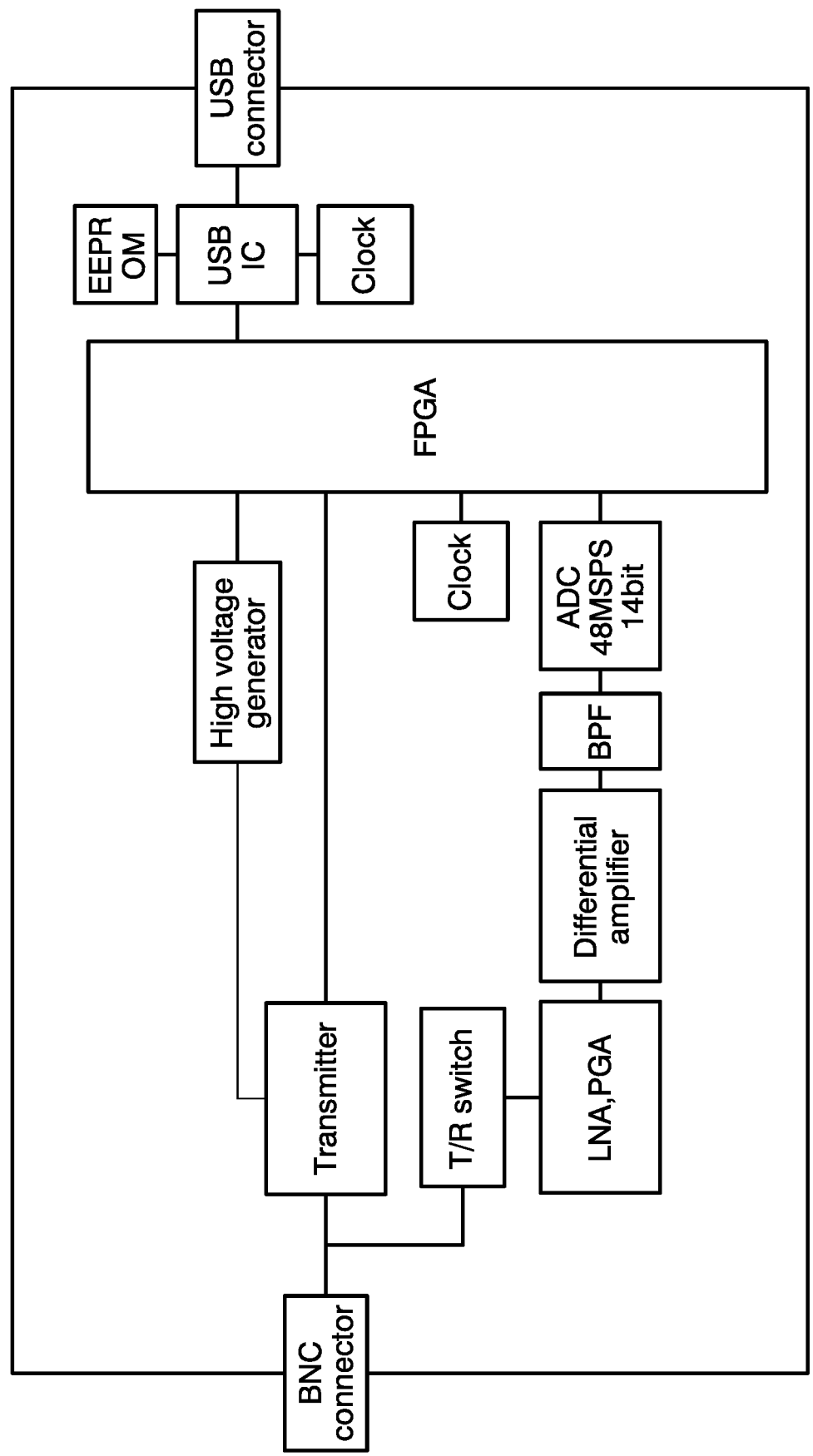
FIGS. 17A and 17B are a schematic block diagram and photo, respectively, showing another embodiment of an ultrasound controller made in accordance with principles of the presently disclosed subject matter.
Figure 17B:
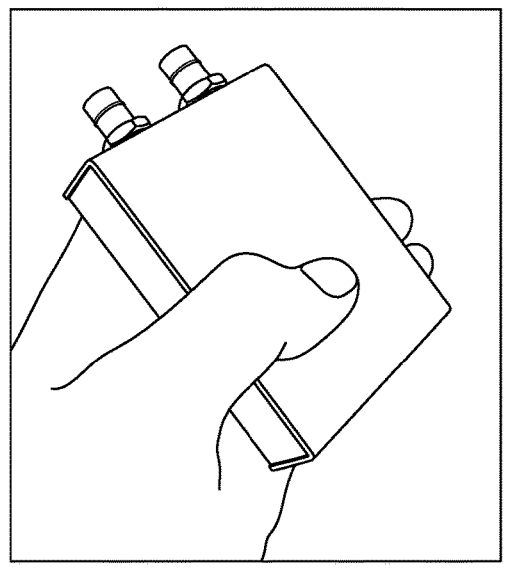

FIGS. 17A and 17B are a schematic block diagram and photo, respectively, showing another embodiment of an ultrasound controller made in accordance with principles of the presently disclosed subject matter. The ultrasound controller can include or can consist of a field-programmable gate array (FPGA), high voltage generator, transmitter, T/R switch, Low-noise amplifier (LNA), Programmable Gain Amplifier (PGA), Differential amplifier, Band pass filter (BPF), Analog digital converter (ADC), probe connector, communication interface connector, and other components. The ultrasound probe can be connected to the BNC connector as shown in FIG. 17A. The transmitter can generate a substantially 2 MHz high voltage burst pulse (+/−4V~25V). The T/R switch can remove the transmitted high voltage burst pulse signal and extract the reflected ultrasound signal from brain (and other) tissue. Amplifiers (LNA, PGA and differential amplifier) can be provided to increase the signal voltage (−4 dB~+36 dB). ADC digitizes the signal. In this diagram, IQ demodulation is accomplished in FPGA (digital IQ demodulation). The RF data or IQ data is transmitted to the patient monitor (FIG. 16) via a communication cable such as a USB wire or via wireless transmission.

Figure 18A:
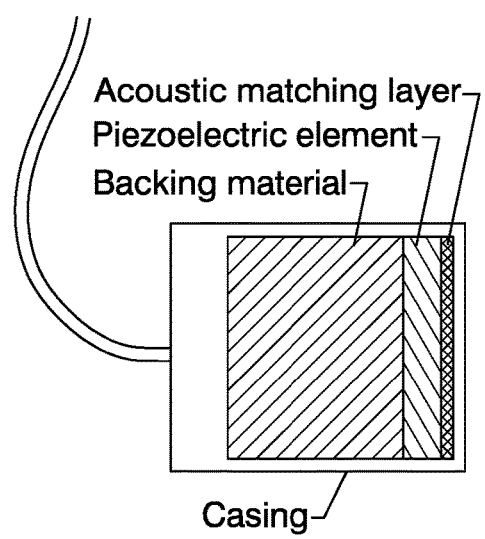
FIGS. 18A and 18B are a schematic diagram and photo, respectively, showing another embodiment of an ultrasound probe made in accordance with principles of the presently disclosed subject matter.
Figure 18B:
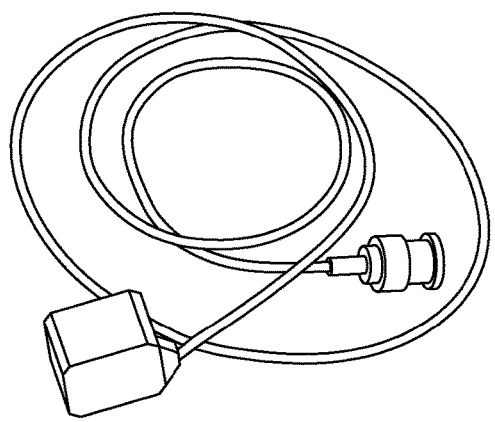

FIGS. 18A and 18B are a schematic diagram and photo, respectively, showing another embodiment of an ultrasound probe made in accordance with principles of the presently disclosed subject matter. The ultrasound probe can include or consist of a piezoelectric element, a backing material, an acoustic matching layer, and casing.

During use, a high voltage burst pulse is generated by a transmitter in the ultrasound controller (FIG. 16), and is applied to the piezoelectric element in the ultrasound probe. The piezoelectric element then oscillates by repeatedly expanding and contracting, generating an ultrasound wave. When the element receives a vibration (or an ultrasonic wave) reflected from the target tissue, the piezoelectric element generates a voltage that correlates with an image of the target tissue.

The backing material is located behind the piezoelectric element and is configured to prevent excessive vibration and to control the vibration signature output by the piezoelectric element. The shape and material choice for the backing material can be selected to shorten the pulse length of the ultrasonic wave generated by the piezoelectric element.

Ultrasonic waves transmitted from the piezoelectric element can be prevented from transmission through and/or to a target tissue due to reflection off of adjacent tissue including target tissue because there is a difference in acoustic impedance between the piezoelectric element and the adjacent tissue or object. To avoid this phenomenon, and to ensure deep penetration of the ultrasonic wave to or into target tissue, an intermediate material (acoustic matching layer) can be inserted between the piezoelectric element and the target tissue so that ultrasonic waves can efficiently enter the object and/or target tissue. An acoustic lens can also be provided adjacent the piezoelectric element and configured to focus the beam of the generated ultrasonic wave towards the target tissue.

While the subject matter has been described in detail with reference to exemplary embodiments thereof, it will be apparent to one skilled in the art that various changes can be made, and equivalents employed, without departing from the scope of the invention. In particular, the various features from each of the disclosed specific embodiments can be interchanged or incorporated into each of the other disclosed embodiments disclosed herein without departing from the spirit and scope of the invention. All related art references including U.S. and foreign patents and patent publications described above are hereby incorporated by reference in their entirety.

What is claimed is:

1. An apparatus for determining at least one of brain swelling and shifting in a patient, comprising:
   an attachment structure configured to attach an ultrasound transducer to a head, with skull, adjacent the brain of the patient; and
   a controller configured to receive information indicating location of a first brain tissue portion relative to a second brain tissue portion by the ultrasound transducer and to determine whether an intracranial pressure of the patient increases based on change over time of the information, the change over time of the information representing a displacement of position over time of the first brain tissue portion relative to the second brain tissue portion,
   wherein the controller is configured to determine whether the at least one of brain swelling and shifting has occurred based on a determination of whether the change over time of the information is within a predetermined target amount;

at least one of position and orientation of the skull of the patient monitored by an accelerometer and represented by data from such monitoring, the controller is configured to determine variance of (a) the at least one of position and orientation of the skull as represented by the data from the monitoring performed by the accelerometer, relative to (b) the change over time of the information; and the controller is configured to calculate the displacement of position over time, of the first brain tissue portion relative to the second brain tissue portion, based on IQ data, the IQ data included in the information.

2. The apparatus of claim 1, further comprising an elastic band configured to secure the ultrasound transducer.

3. The apparatus of claim 1, wherein
the controller is further configured to remove data sensed by the ultrasound transducer due to at least one of a cardiac cycle and a respiratory cycle of the patient.

4. The apparatus of claim 1, wherein
the controller is configured to calculate displacement of brain tissue utilizing the following formula:

displacement'($t$)=theta'($t$)*lambda/2/2pi−theta'($t$0) *lambda/2/2pi; and theta'($t$)☐ arg($IQ$data($t$)−$IQ$ centerpoint), where:
displacement'(t) is tissue displacement (swelling/shifting) from IQ center point;
theta'(t) is IQplot argument (IQ phase angle) from IQ centerpoint;
IQdata(t) is IQ data at time t; and
IQ centerpoint is IQ trajectory center point.

5. The apparatus of claim 1, further comprising:
a patient monitor including a casing and a video display, the patient monitor configured to monitor patient parameters including SpO2, CO2, and Blood Pressure, wherein
the controller is located within the casing of the patient monitor, and the ultrasound transducer is connected to the patient monitor via at least one of a wired and wireless connection, and
the controller is configured to create at least one of brain swelling data and brain shifting data from the calculated displacement of brain tissue, and to show the at least one of brain swelling data and brain shifting data on the video display.

6. The apparatus of claim 5, further comprising:
an alarm mechanism configured to provide at least one of an audible and visual signal when the at least one of brain swelling data and brain shifting data is in an abnormal situation.

7. The apparatus of claim 1, wherein the ultrasound controller includes a field-programmable gate array (FPGA), a high voltage generator, a transmitter, T/R switch, a Low-noise amplifier (LNA), a Programmable Gain Amplifier (PGA), a Differential amplifier, a Band pass filter (BPF), an Analog digital converter (ADC), a transducer connector, and a communication interface connector.

8. The apparatus of claim 1, further comprising:
a patient monitor, wherein the controller is incorporated into the patient monitor, and
the patient monitor is configured to connect the ultrasound transducer to the patient monitor via one of wireless and wired connection.

9. The apparatus of claim 1, wherein
the controller is configured to provide an alarm when an increase above a target amount in the location of the first brain tissue portion relative to the second brain tissue portion is determined, and
the patient is treated for increased intracranial pressure after the alarm is provided.

10. The apparatus of claim 4, further comprising:
a patient monitor including a casing and a video display, the patient monitor configured to monitor patient parameters including SpO2, CO2, and Blood Pressure, wherein
the controller is located within the casing of the patient monitor, and the ultrasound transducer is connected to the patient monitor via at least one of a wired and wireless connection, and
the controller is configured to create at least one of brain swelling data and brain shifting data from the calculated displacement of brain tissue, and to show the at least one of brain swelling data and brain shifting data on the video display.

11. The apparatus of claim 10, further comprising:
an alarm mechanism configured to provide at least one of an audible and visual signal when the at least one of brain swelling data and brain shifting data is in an abnormal situation.

12. The apparatus of claim 4, wherein the ultrasound controller includes a field-programmable gate array (FPGA), a high voltage generator, a transmitter, T/R switch, a Low-noise amplifier (LNA), a Programmable Gain Amplifier (PGA), a Differential amplifier, a Band pass filter (BPF), an Analog digital converter (ADC), a transducer connector, and a communication interface connector.

13. The apparatus of claim 4, further comprising:
a patient monitor, wherein the controller is incorporated into the patient monitor, and
the patient monitor is configured to connect the ultrasound transducer to the patient monitor via one of wireless and wired connection.

14. The apparatus of claim 4, wherein
the controller is configured to provide an alarm when an increase above a target amount in the location of the first brain tissue portion relative to the second brain tissue portion is determined, and
the patient is treated for increased intracranial pressure after the alarm is provided.

15. The apparatus of claim 1, wherein
the controller is configured to determine that the brain is floating normally in a cerebrospinal fluid when the information is functionally coordinated with the at least one of position and orientation of the skull of the patient which is monitored by the accelerometer.

16. An apparatus for determining at least one of brain swelling and shifting in a patient, comprising:
an attachment structure configured to attach an ultrasound transducer to a head adjacent the brain of the patient; and
a controller configured to receive information indicating location of a first brain tissue portion relative to a second brain tissue portion by the ultrasound transducer and to determine whether an intracranial pressure of the patient increases based on change over time of the information, the change over time of the information representing a displacement of position over time of the first brain tissue portion relative to the second brain tissue portion, movement of the head and chest monitored by an accelerometer and represented by data, the accelerometer attached to the head and the chest of the patient;

the controller is configured to use the data, from such monitoring performed by the accelerometer, to calculate positional relationship between the first brain tissue portion and the second brain tissue portion, and the controller is configured to calculate the displacement of position over time, of the first brain tissue portion relative to the second brain tissue portion, based on IQ data, and the IQ data included in the information.

17. A measuring apparatus configured to measure a brain tissue displacement of a patient, the measuring apparatus comprising:

a circuitry, provided in a controller, the circuitry:

configured to input a signal received from an ultrasound transducer, the ultrasound transducer communicatively connected to the controller via wires or via a wireless communication device;

configured to separate the signal received from the ultrasound transducer attached to a head of the patient by quadrature detection into a first signal component and a second signal component;

configured to determine a center point of an arc-shaped trajectory formed by change over time of the first and second signal components on a coordinate plane in which a first coordinate axis corresponds to the first signal component and a second coordinate axis corresponds to the second signal component;

configured to calculate a displacement amount of a brain tissue of the patient based on change over time of a phase angle between the first and second signal components, which is determined based on the center point;

configured to create at least one of brain swelling and brain shifting data; and configured to output the at least one of brain swelling and brain shifting data to a video display, so as to be displayed on the video display.

18. The measuring apparatus according to claim 17, wherein the controller is configured to remove, from the signal, a clutter signal that causes a shift of the center point from an origin of the coordinate plane.

19. The measuring apparatus according to claim 17, wherein the controller is configured to determine the center point at every at least one of cardiac cycle and respiratory cycle.

* * * * *